United States Patent
Connor

(10) Patent No.: US 11,662,819 B2
(45) Date of Patent: May 30, 2023

(54) METHOD FOR INTERPRETING A WORD, PHRASE, AND/OR COMMAND FROM ELECTROMAGNETIC BRAIN ACTIVITY

(71) Applicant: Robert A. Connor, St. Paul, MN (US)

(72) Inventor: Robert A. Connor, St. Paul, MN (US)

(73) Assignee: Medibotics, St. Paul, MN (US)

( * ) Notice: Subject to any disclaimer, the term of this patent is extended or adjusted under 35 U.S.C. 154(b) by 0 days.

(21) Appl. No.: 17/665,086

(22) Filed: Feb. 4, 2022

(65) Prior Publication Data

US 2022/0155867 A1    May 19, 2022

Related U.S. Application Data

(63) Continuation-in-part of application No. 17/136,117, filed on Dec. 29, 2020, which is a continuation-in-part of application No. 16/554,029, filed on Aug. 28, 2019, said application No. 17/136,117 is a continuation-in-part of application No. 16/554,029, filed on Aug. 28, 2019, which is a
(Continued)

(51) Int. Cl.
| | |
|---|---|
| *G06F 3/01* | (2006.01) |
| *G10L 15/22* | (2006.01) |
| *G06F 3/041* | (2006.01) |
| *G06F 3/02* | (2006.01) |

(52) U.S. Cl.
CPC .............. *G06F 3/015* (2013.01); *G06F 3/013* (2013.01); *G06F 3/017* (2013.01); *G06F 3/02* (2013.01); *G06F 3/041* (2013.01); *G10L 15/22* (2013.01); *G10L 2015/223* (2013.01)

(58) Field of Classification Search
CPC .......... G06F 3/015; G06F 3/013; G06F 3/017; G06F 3/02; G06F 3/041; G06F 2203/0381; G10L 15/22; G10L 2015/223; G16H 20/30; G16H 40/63; A61B 5/6803; A61B 5/291; G02C 5/14; G02C 11/10
See application file for complete search history.

(56) References Cited

U.S. PATENT DOCUMENTS

| | | |
|---|---|---|
| 3,998,213 A | 12/1976 | Price |
| 4,697,598 A | 10/1987 | Bernard et al. |
| (Continued) | | |

OTHER PUBLICATIONS

Vilimek et al., "BC (eye): Combining eye-gaze input with brain-computer interaction." International Conference on Universal Access in Human-Computer Interaction. Springer (Year: 2009).*
(Continued)

*Primary Examiner* — Jacqueline Cheng
*Assistant Examiner* — Tho Q Tran

(57) ABSTRACT

This invention is a non-invasive Brain to Computer Interface (BCI) method for interpreting a word, phrase, or command from brain activity by identifying a pattern of electromagnetic brain activity which occurs when a person uses different action modalities to communicate a word, phrase, or command. This method can enable people with neuromuscular limitations and/or paralysis to communicate. It can also enable people to communicate and/or to control environmental devices via their thought patterns in situations where communication via touch screen, keyboard, mouse, voice command, or gesture recognition is not appropriate and/or possible.

10 Claims, 16 Drawing Sheets

Related U.S. Application Data continuation-in-part of application No. 16/022,987, filed on Jun. 29, 2018, now Pat. No. 11,172,859, which is a continuation-in-part of application No. 15/136,948, filed on Apr. 24, 2016, now Pat. No. 10,234,942.

(60) Provisional application No. 62/972,692, filed on Feb. 11, 2020, provisional application No. 62/851,904, filed on May 23, 2019, provisional application No. 62/796,901, filed on Jan. 25, 2019, provisional application No. 62/791,838, filed on Jan. 13, 2019, provisional application No. 62/322,594, filed on Apr. 14, 2016, provisional application No. 62/303,126, filed on Mar. 3, 2016, provisional application No. 62/169,661, filed on Jun. 2, 2015, provisional application No. 62/160,172, filed on May 12, 2015.

(56) References Cited

U.S. PATENT DOCUMENTS

| | | |
|---|---|---|
| 4,709,702 A | 12/1987 | Sherwin |
| 4,770,180 A | 9/1988 | Schmidt et al. |
| 4,836,219 A | 6/1989 | Hobson et al. |
| 4,967,038 A | 10/1990 | Gevins et al. |
| 5,038,782 A | 8/1991 | Gevins et al. |
| 5,293,867 A | 3/1994 | Oommen |
| 5,479,934 A | 1/1996 | Imran |
| 5,740,812 A | 4/1998 | Cowan |
| 5,800,351 A | 9/1998 | Mann |
| 5,954,667 A | 9/1999 | Finkenzeller et al. |
| 6,001,065 A | 12/1999 | Devito |
| 6,067,464 A | 5/2000 | Musha |
| 6,154,669 A | 11/2000 | Hunter et al. |
| 6,161,030 A | 12/2000 | Levendowski et al. |
| 6,167,298 A | 12/2000 | Levin |
| 6,171,258 B1 | 1/2001 | Karakasoglu et al. |
| 6,254,536 B1 | 7/2001 | Devito |
| 6,381,481 B1 | 4/2002 | Levendowski et al. |
| 6,488,617 B1 | 12/2002 | Katz |
| 6,574,513 B1 | 6/2003 | Collura et al. |
| 6,811,538 B2 | 11/2004 | Westbrook et al. |
| 7,158,822 B2 | 1/2007 | Payne, Jr. |
| 7,297,119 B2 | 11/2007 | Westbrook et al. |
| 7,344,244 B2 | 3/2008 | Goodall et al. |
| D565,735 S | 4/2008 | Washbon |
| 7,390,088 B2 | 6/2008 | Goodall et al. |
| 7,486,988 B2 | 2/2009 | Goodall et al. |
| 7,551,952 B2 | 6/2009 | Gevins et al. |
| 7,689,274 B2 | 3/2010 | Mullen et al. |
| 7,885,706 B2 | 2/2011 | Ludvig et al. |
| 8,103,328 B2 | 1/2012 | Turner et al. |
| 8,244,342 B2 | 8/2012 | Goodall et al. |
| 8,271,075 B2 | 9/2012 | Chuang et al. |
| 8,301,218 B2 | 10/2012 | Nguyen et al. |
| 8,346,354 B2 | 1/2013 | Hyde et al. |
| 8,355,769 B2 | 1/2013 | Levendowski et al. |
| 8,392,250 B2 | 3/2013 | Pradeep et al. |
| 8,392,251 B2 | 3/2013 | Pradeep et al. |
| 8,396,744 B2 | 3/2013 | Pradeep et al. |
| 8,463,354 B2 | 6/2013 | Fadem |
| 8,467,133 B2 | 6/2013 | Miller |
| 8,472,120 B2 | 6/2013 | Border et al. |
| 8,477,425 B2 | 7/2013 | Border et al. |
| 8,482,859 B2 | 7/2013 | Border et al. |
| 8,488,246 B2 | 7/2013 | Border et al. |
| 8,548,852 B2 | 10/2013 | Pradeep et al. |
| 8,562,540 B2 | 10/2013 | Goodall et al. |
| 8,639,313 B2 | 1/2014 | Westbrook et al. |
| 8,655,428 B2 | 2/2014 | Pradeep et al. |
| 8,812,075 B2 | 8/2014 | Nguyen et al. |
| 2001/0056225 A1 | 12/2001 | DeVito |
| 2002/0029005 A1 | 3/2002 | Levendowski et al. |
| 2002/0165462 A1 | 11/2002 | Westbrook et al. |
| 2002/0188216 A1 | 12/2002 | Kayyali et al. |
| 2003/0018278 A1 | 1/2003 | Jordan |
| 2004/0267152 A1 | 12/2004 | Pineda |
| 2005/0027207 A1 | 2/2005 | Westbrook et al. |
| 2005/0277821 A1 | 12/2005 | Payne |
| 2006/0252978 A1 | 11/2006 | Vesely et al. |
| 2006/0252955 A1 | 11/2006 | Vesely et al. |
| 2007/0010757 A1 | 1/2007 | Goodall et al. |
| 2007/0019279 A1 | 1/2007 | Goodall et al. |
| 2007/0093706 A1 | 4/2007 | Gevins et al. |
| 2007/0106145 A1 | 5/2007 | Kim et al. |
| 2007/0106169 A1 | 5/2007 | Fadem |
| 2007/0112262 A1 | 5/2007 | Payne |
| 2007/0191727 A1 | 8/2007 | Fadem |
| 2007/0225585 A1 | 9/2007 | Washbon et al. |
| 2007/0238945 A1 | 10/2007 | Delic et al. |
| 2007/0249952 A1 | 10/2007 | Rubin et al. |
| 2008/0082019 A1 | 4/2008 | Ludving et al. |
| 2008/0161673 A1 | 7/2008 | Goodall et al. |
| 2008/0177197 A1 | 7/2008 | Lee et al. |
| 2008/0208072 A1 | 8/2008 | Fadem et al. |
| 2009/0088619 A1 | 4/2009 | Turner et al. |
| 2009/0105576 A1 | 4/2009 | Do et al. |
| 2009/0281446 A2 | 11/2009 | Ludvig et al. |
| 2010/0094154 A1* | 4/2010 | Schalk .................. A61B 5/398 |
| | | 600/544 |
| 2010/0099954 A1 | 4/2010 | Dickinson et al. |
| 2010/0125190 A1 | 5/2010 | Fadem |
| 2010/0240982 A1 | 9/2010 | Westbrook et al. |
| 2011/0015503 A1 | 1/2011 | Joffe et al. |
| 2011/0028798 A1 | 2/2011 | Hyde et al. |
| 2011/0029038 A1 | 2/2011 | Hyde et al. |
| 2011/0029044 A1 | 2/2011 | Hyde et al. |
| 2011/0098593 A1 | 4/2011 | Low et al. |
| 2011/0221656 A1 | 9/2011 | Haddick et al. |
| 2011/0221669 A1 | 9/2011 | Shams et al. |
| 2011/0221672 A1 | 9/2011 | Osterhout et al. |
| 2011/0222745 A1 | 9/2011 | Osterhout et al. |
| 2011/0227820 A1 | 9/2011 | Haddick et al. |
| 2011/0237971 A1 | 9/2011 | Pradeep et al. |
| 2011/0270117 A1 | 11/2011 | Warwick et al. |
| 2011/0282231 A1 | 11/2011 | Pradeep et al. |
| 2011/0282232 A1 | 11/2011 | Pradeep et al. |
| 2012/0022391 A1* | 1/2012 | Leuthardt .................. A61F 4/00 |
| | | 600/544 |
| 2012/0029379 A1 | 2/2012 | Sivadas |
| 2012/0062445 A1 | 3/2012 | Haddick et al. |
| 2012/0072289 A1 | 3/2012 | Pradeep et al. |
| 2012/0075168 A1 | 3/2012 | Osterhout et al. |
| 2012/0090003 A1* | 4/2012 | Dove ................ H04N 21/42201 |
| | | 725/38 |
| 2012/0150545 A1 | 6/2012 | Simon |
| 2012/0212398 A1 | 8/2012 | Border et al. |
| 2012/0212400 A1 | 8/2012 | Border et al. |
| 2012/0218172 A1 | 8/2012 | Border et al. |
| 2012/0218301 A1 | 8/2012 | Miller |
| 2012/0226127 A1 | 9/2012 | Asjes et al. |
| 2012/0235883 A1 | 9/2012 | Border et al. |
| 2012/0235886 A1 | 9/2012 | Border et al. |
| 2012/0235887 A1 | 9/2012 | Border et al. |
| 2012/0235900 A1 | 9/2012 | Border et al. |
| 2012/0236030 A1 | 9/2012 | Border et al. |
| 2012/0242678 A1 | 9/2012 | Border et al. |
| 2012/0242698 A1 | 9/2012 | Haddick et al. |
| 2013/0046206 A1 | 2/2013 | Preminger |
| 2013/0056010 A1 | 3/2013 | Walker et al. |
| 2013/0060097 A1 | 3/2013 | Rubin |
| 2013/0127708 A1 | 5/2013 | Jung et al. |
| 2013/0127980 A1 | 5/2013 | Haddick et al. |
| 2013/0131464 A1 | 5/2013 | Westbrook et al. |
| 2013/0131537 A1 | 5/2013 | Tam |
| 2013/0177883 A1 | 7/2013 | Barnehama et al. |
| 2013/0185144 A1 | 7/2013 | Pradeep et al. |
| 2013/0242262 A1 | 9/2013 | Lewis |
| 2013/0303837 A1 | 11/2013 | Berka et al. |
| 2013/0310676 A1 | 11/2013 | Jung |
| 2013/0314243 A1 | 11/2013 | Le |
| 2013/0314303 A1 | 11/2013 | Osterhout et al. |
| 2013/0317382 A1 | 11/2013 | Le |

(56) References Cited

U.S. PATENT DOCUMENTS

| | | |
|---|---|---|
| 2013/0317384 A1 | 11/2013 | Le |
| 2013/0338446 A1 | 12/2013 | Van Vugt et al. |
| 2014/0023999 A1 | 1/2014 | Greder |
| 2014/0267005 A1 | 9/2014 | Urbach |
| 2014/0267401 A1 | 9/2014 | Urbach |
| 2014/0316230 A1 | 10/2014 | Denison et al. |
| 2014/0347265 A1 | 11/2014 | Aimone et al. |
| 2014/0375545 A1 | 12/2014 | Ackerman et al. |
| 2015/0338917 A1* | 11/2015 | Steiner ................. H04L 9/3271 345/156 |
| 2017/0281086 A1* | 10/2017 | Donaldson ......... A61B 5/14542 |
| 2019/0295566 A1* | 9/2019 | Moghadamfalahi ... A61B 5/318 |

OTHER PUBLICATIONS

Erp et al., "Touch-based Brain Computer Interfaces: State of the art," 2014 IEEE Haptics Symposium (Haptics), 2014, pp. 397-401 (Year: 2014).*

Pfurtscheller et al. (Motor Imagery and Direct Brain-Computer Communication, Proceedings of the IEEE, vol. 89, No. 7) (Year: 2001).*

McFarland et al. (Mu and beta rhythm topographies during motor imagery and actual movements Abstract, Brain Topogr., vol. 12(3), pp. 177-186) (Year: 2000).*

Martinez-Leon et al. (Are low cost Brain Computer Interface headsets ready for motor imagery applications?, Expert Systems with Applications vol. 49, 1, pp. 136-144) (Year: 2016).*

\* cited by examiner

METHOD FOR INTERPRETING A WORD, PHRASE, AND/OR COMMAND FROM ELECTROMAGNETIC BRAIN ACTIVITY

CROSS-REFERENCE TO RELATED APPLICATIONS

This application is a continuation-in-part of U.S. patent application Ser. No. 17/136,117 filed on Dec. 29, 2020. This application is a continuation-in-part of U.S. patent application Ser. No. 16/554,029 filed on Aug. 28, 2019.

U.S. patent application Ser. No. 17/136,117 claimed the priority benefit of U.S. provisional patent application 62/972,692 filed on Feb. 11, 2020. U.S. patent application Ser. No. 17/136,117 was a continuation-in-part of U.S. patent application Ser. No. 16/554,029 filed on Aug. 28, 2019.

U.S. patent application Ser. No. 16/554,029 claimed the priority benefit of U.S. provisional patent application 62/851,904 filed on May 23, 2019. U.S. patent application Ser. No. 16/554,029 claimed the priority benefit of U.S. provisional patent application 62/796,901 filed on Jan. 25, 2019. U.S. patent application Ser. No. 16/554,029 claimed the priority benefit of U.S. provisional patent application 62/791,838 filed on Jan. 13, 2019. U.S. patent application Ser. No. 16/554,029 was a continuation-in-part of U.S. patent application Ser. No. 16/022,987 filed on Jun. 29, 2018 which issued as U.S. Pat. No. 11,172,859 on Nov. 15, 2021.

U.S. patent application Ser. No. 16/022,987 was a continuation-in-part of U.S. patent application Ser. No. 15/136,948 filed on Apr. 24, 2016 which issued as U.S. Pat. No. 10,234,942 on Mar. 19, 2019.

U.S. patent application Ser. No. 15/136,948 claimed the priority benefit of U.S. provisional patent application 62/322,594 filed on Apr. 14, 2016. U.S. patent application Ser. No. 15/136,948 claimed the priority benefit of U.S. provisional patent application 62/303,126 filed on Mar. 3, 2016. U.S. patent application Ser. No. 15/136,948 claimed the priority benefit of U.S. provisional patent application 62/169,661 filed on Jun. 2, 2015. U.S. patent application Ser. No. 15/136,948 claimed the priority benefit of U.S. provisional patent application 62/160,172 filed on May 12, 2015.

The entire contents of these applications are incorporated herein by reference.

FEDERALLY SPONSORED RESEARCH

Not Applicable

SEQUENCE LISTING OR PROGRAM

Not Applicable

BACKGROUND

Field of Invention

This invention relates to methods for interpreting electromagnetic brain activity.

Introduction

This invention relates to non-invasive Brain Computer Interface (BCI) methods for monitoring and interpreting electromagnetic energy from a person's brain. The non-invasive BCI methods disclosed herein can enable people with neuromuscular limitations and/or paralysis to communicate with other people or to control environmental devices via their thought patterns. The non-invasive BCI methods disclosed herein can also enable people to communicate with other people or to control environmental devices via their thought patterns in situations where more conventional modalities (such as touch screen, keyboard, mouse, voice command, or gesture recognition) are not appropriate or not possible.

Review of the Relevant Art

It can be challenging trying to classify relevant art in this field into discrete categories. However, classification of relevant art into categories, even if imperfect, can be an invaluable tool for reviewing the relevant art. Towards this end, I herein identify 12 categories of relevant art and provide examples of relevant art in each category (including patent or patent application number, inventor, publication date, and title). Some examples of relevant art disclose multiple concepts and thus appear in more than one category.

The 12 categories of relevant art which are used for this review are as follows: (1) device with [multiple] front-to-back arcuate members and EEG/brainwave sensors; (2) device with [multiple] side-to-side arcuate members and EEG/brainwave sensors; (3) device with multiple cross-crossing arcuate members and EEG/brainwave sensors; (4) device with multiple arms radially-extending from side and EEG/brainwave sensors; (5) device with multiple arms radially-downward from top and EEG/brainwave sensors; (6) device with multiple arms radially-forward from rear and EEG/brainwave sensors; (7) device with multiple arms radially-backward from front and EEG/brainwave sensors; (8) device with circular horizontal loop (e.g. headband style) and EEG/brainwave sensors; (9) device with top semicircular loop (e.g. headphone style) and EEG/brainwave sensors; (10) device with rear semicircular loop and EEG/brainwave sensors; (11) device with frontal semicircular loop and EEG/brainwave sensors; and (12) device like eyeglasses or other eyewear with EEG/brainwave sensors.

I have labeled this section as a review of the relevant art, instead of a review of the prior art, for two reasons. First, some of the art included in this review has a priority date after the priority date of this disclosure, so I do not wish to call all of this art "prior." Second, some of the examples in this present disclosure can be classified into one or more of these categories but are nonetheless novel, so I do not wish to imply that all of the art in these categories is "prior". These caveats notwithstanding, I hope that the reader finds this review and categorization of the relevant art to be useful.

1. Device with [Multiple] Front-to-Back Arcuate Member(s) and EEG/Brainwave Sensor(s)

Devices in this category hold electromagnetic brain activity sensors in contact with (or proximity to) a person's head using (multiple) arcing member(s) which span a person's head from front-to-back (or vice versa). Devices in this category can look similar to some types of bicycle helmets with front-to-back arcuate members. In an example, the front-to-back arcing members can converge at the forehead and at the rear of the head. In an example, a device in this category can comprise: a first arcuate member which encircles a person's head: a second arcuate member which loops front-to-back over the top of the head; and third and fourth arcuate members which loop front-to-back over the sides of the head between the first and second members. Devices in this category can hold a relatively large number of electromagnetic brain activity sensors along arcuate front-to-rear lines on a person's head. However, such devices tend to be too obtrusive to wear during the activities of daily life.

Prior art which appears to be within this category includes U.S. Pat. No. 3,998,213 (Price, Dec. 21, 1976, "Self-Adjustable Holder for Automatically Positioning Electroencephalographic Electrodes"), U.S. Pat. No. 8,355,769 (Levendowski et al., Jan. 15, 2013, "System for the Assessment of Sleep Quality in Adults and Children"), U.S. Pat. No. 8,463,354 (Fadem, Jun. 11, 2013, "Electrode System with Rigid-Flex Circuit"), U.S. Pat. No. 8,639,313 (Westbrook et al, Jan. 28, 2014, "System for the Assessment of Sleep Quality in Adults and Children"); and U.S. patent applications 20100125190 (Fadem, May 20, 2010, "Electrode System"), 20100240982 (Westbrook et al., Sep. 23, 2010, "System for the Assessment of Sleep Quality in Adults and Children"), and 20130131464 (Westbrook et al., May 23, 2013, "System for the Assessment of Sleep Quality in Adults and Children").

2. Device with [Multiple] Side-to-Side Arcuate Member(s) and EEG/Brainwave Sensor(s)

Devices in this category hold electromagnetic brain activity sensors in contact with (or proximity to) a person's head using (multiple) arcing member(s) which span a person's head from side to side. In an example, side-to-side arcing members can converge near, or over, the person's ears. In an example, devices in this category can be similar to those in the previous category, except having been rotated 90 degrees so that the arcuate members converge on the sides of the person's head rather than the front and rear of the person's head. Devices in this category can hold a relatively large number of electromagnetic brain activity sensors along arcuate side-to-side lines on a person's head. However, such devices tend to be too obtrusive to wear during the activities of daily life.

Prior art which appears to be within this category includes U.S. Pat. No. 4,836,219 (Hobson et al., Jun. 6, 1989, "Electronic Sleep Monitor Headgear"), U.S. Pat. No. 5,800,351 (Mann, Sep. 1, 1998, "Electrode Supporting Head Set"), U.S. Pat. No. 6,574,513 (Collura et al., Jun. 3, 2003, "EEG Electrode Assemblies"), U.S. Pat. No. 7,158,822 (Payne Jr., Jan. 2, 2007, "Electrode Holder, Headwear, and Wire Jacket Adapted for Use in Sleep Apnea Testing"), and U.S. Pat. No. 7,885,706 (Ludvig et al., Feb. 8, 2011, "System and Device for Seizure Detection").

Prior art which appears to be within this category also includes U.S. patent applications: 20030018278 (Jordan, Jan. 23, 2003, "Electroencephalogram Acquisition Unit and System"), 20050277821 (Payne, Dec. 15, 2005, "Electrode Holder, Headwear, and Wire Jacket Adapted for Use in Sleep Apnea Testing"), 20070112262 (Payne, May 17, 2007, "Electrode Holder, Headwear, and Wire Jacket Adapted for Use in Sleep Apnea Testing"), 20080082019 (Ludving et al., Apr. 3, 2008, "System and Device for Seizure Detection"), 20090281446 (Ludvig et al., Nov. 12, 2009, "System and Device for Seizure Detection"), 20110015503 (Joffe et al., Jan. 20, 2011, "Medical Apparatus for Collecting Patient Electroencephalogram (EEG) Data"), and 20110270117 (Warwick et al., Nov. 3, 2011, "Remote Continuous Seizure Monitor and Alarm").

3. Device with Multiple Cross-Crossing Arcuate Members and EEG/Brainwave Sensor(s)

Devices in this category hold electromagnetic brain activity sensors in contact with (or proximity to) a person's head using multiple arcing members which span a person's head from front-to-rear and also multiple arcing members which span a person's head from side-to-side. In an example, the front-to-rear arcuate members and the side-to-side arcuate members can form a criss-cross pattern on the person's head. Devices in this category can hold a relatively large number of electromagnetic brain activity sensors on a person's head. However, such devices tend to be too obtrusive to wear during the activities of daily life.

Prior art which appears to be within this category includes U.S. Pat. No. 3,998,213 (Price, Dec. 21, 1976, "Self-Adjustable Holder for Automatically Positioning Electroencephalographic Electrodes"), U.S. Pat. No. 5,293,867 (Oommen, Mar. 15, 1994, "Method and Apparatus for Marking Electrode Locations for Electroencephalographic Procedure"), U.S. Pat. No. 5,479,934 (Imran, Jan. 2, 1996, "EEG Headpiece with Disposable Electrodes and Apparatus and System and Method for Use Therewith"), U.S. Pat. No. 6,488,617 (Katz, Dec. 3, 2002, "Method and Device for Producing a Desired Brain State"), U.S. Pat. No. 8,463,354 (Fadem, Jun. 11, 2013, "Electrode System with Rigid-Flex Circuit"); and U.S. patent applications 20030018278 (Jordan, Jan. 23, 2003, "Electroencephalogram Acquisition Unit and System"), and 20100125190 (Fadem, May 20, 2010, "Electrode System").

4. Device with Multiple Arms Radially-Extending from Side and EEG/Brainwave Sensor(s)

Devices in this category hold electromagnetic brain activity sensors in contact with (or proximity to) a person's head using multiple sensor-holding protrusions, fingers, or arms which extend radially outward from a central position on one side (or from central positions on both sides) of a person's head. In an example, such devices can include bilateral clusters (one on each side of the head) of radially-extending protrusions, fingers, or arms. In an example, radially-extending protrusions, fingers, or arms can curve around the head toward the front, top, and/or rear portions of the head. To use colorful language, some such devices can look like a wearer has one or two starfish (or even octopi) clinging to the sides of their head. Such devices can be less obtrusive than those in the preceding categories (especially when they do not span the forehead or the top of the head), but can still attract attention if worn during the activities of daily life.

Prior art which appears to be within this category includes U.S. Pat. No. 5,954,667 (Finkenzeller et al., Sep. 21, 1999, "Device for Deriving Acoustically Evoked Brain Potentials"), U.S. Pat. No. 8,271,075 (Chuang et al., Sep. 18, 2012, "Audio Headset with Bio-Signal Sensors"), U.S. Pat. No. 8,392,250 (Pradeep et al., Mar. 5, 2013, "Neuro-Response Evaluated Stimulus in Virtual Reality Environments"), U.S. Pat. No. 8,392,251 (Pradeep et al., Mar. 5, 2013, "Location Aware Presentation of Stimulus Material"), U.S. Pat. No. 8,396,744 (Pradeep et al., Mar. 12, 2013, "Effective Virtual Reality Environments for Presentation of Marketing Materials"), U.S. Pat. No. 8,548,852 (Pradeep et al., Oct. 1, 2013, "Effective Virtual Reality Environments for Presentation of Marketing Materials"), and U.S. Pat. No. 8,655,428 (Pradeep et al., Feb. 18, 2014, "Neuro-Response Data Synchronization").

Prior art which appears to be within this category also includes U.S. patent applications: 20070106169 (Fadem, May 10, 2007, "Method and System for an Automated E.E.G. System for Auditory Evoked Responses"), 20070191727 (Fadem, Aug. 16, 2007, "Evoked Response Testing System for Neurological Disorders"), 20070225585 (Washbon and Delic, Sep. 27, 2007, "Headset for Electrodes"), 20070238945 (Delic et al., Oct. 11, 2007, "Electrode Headset"), 20080208072 (Fadem et al., Aug. 28, 2008, "Biopotential Waveform Data Fusion Analysis and Classification Method"), 20110237971 (Pradeep et al., Sep. 29, 2011, "Discrete Choice Modeling Using Neuro-Response Data"), and 20110282231 (Pradeep et al., Nov. 17, 2011, "Mechanisms for Collecting Electroencephalography Data").

Prior art which appears to be within this category also includes U.S. patent applications: 20110282232 (Pradeep et al., Nov. 17, 2011, "Neuro-Response Data Synchronization"), 20120072289 (Pradeep et al., Mar. 22, 2012, "Biometric Aware Content Presentation"), 20130131537 (Tam, May 23, 2013, "Tong Ren Brainwave Entrainment"), 20130185144 (Pradeep et al., Jul. 18, 2013, "Systems and Methods for Analyzing Neuro-Response Data and Virtual Reality Environments"), 20130314243 (Le, Nov. 28, 2013, "System and Method for Enabling Collaborative Analysis of a Biosignal"), 20130317382 (Le, Nov. 28, 2013, "System and Method for Providing and Aggregating Biosignals and Action Data"), and 20130317384 (Le, Nov. 28, 2013, "System and Method for Instructing a Behavior Change in a User").

5. Device with Multiple Arms Radially-Downward from Top and EEG/Brainwave Sensor(s)

Devices in this category hold electromagnetic brain activity sensors in contact with (or proximity to) a person's head using multiple sensor-holding protrusions, fingers, or arms which extend radially downward from a position on the top of a person's head. In an example, radially-extending protrusions, fingers, or arms can curve around the head toward the front, sides, and/or rear portions of the head. To use the colorful language from the previous category, now a figurative starfish (or octopus) is clinging to the top of the person's head. Such devices can be less obtrusive than some of those in the preceding categories, but can still attract attention if worn during the activities of daily life.

Prior art which appears to be within this category includes U.S. Pat. No. 6,067,464 (Musha, May 23, 2009, "Electrode"), U.S. Pat. No. 6,154,669 (Hunter et al., Nov. 28, 2000, "Headset for EEG Measurements"), U.S. Pat. No. 6,161,030 (Levendowski et al., Dec. 12, 2000, "Portable EEG Electrode Locator Headgear"), U.S. Pat. No. 6,381,481 (Levendowski et al., Apr. 30, 2002, "Portable EEG Electrode Locator Headgear"), U.S. Pat. No. 7,551,952 (Gevins et al., Jun. 23, 2009, "EEG Electrode Headset"), U.S. Pat. No. 8,103,328 (Turner et al., Jan. 24, 2012, "Self-Locating Sensor Mounting Apparatus"), U.S. Pat. No. 8,392,250 (Pradeep et al., Mar. 5, 2013, "Neuro-Response Evaluated Stimulus in Virtual Reality Environments"), U.S. Pat. No. 8,392,251 (Pradeep et al., Mar. 5, 2013, "Location Aware Presentation of Stimulus Material"), U.S. Pat. No. 8,396,744 (Pradeep et al., Mar. 12, 2013, "Effective Virtual Reality Environments for Presentation of Marketing Materials"), U.S. Pat. No. 8,548,852 (Pradeep et al., Oct. 1, 2013, "Effective Virtual Reality Environments for Presentation of Marketing Materials"), and U.S. Pat. No. 8,655,428 (Pradeep et al., Feb. 18, 2014, "Neuro-Response Data Synchronization").

Prior art which appears to be within this category also includes U.S. patent applications: 20020029005 (Levendowski et al., Mar. 7, 2002, "Portable EEG Electrode Locator Headgear"), 20070093706 (Gevins et al., Apr. 26, 2007, "EEG Electrode Headset"), 20090088619 (Turner et al., Apr. 2, 2009, "Self-Locating Sensor Mounting Apparatus"), 20110098593 (Low et al., Apr. 28, 2011, "Head Harness & Wireless EEG Monitoring System"), 20110237971 (Pradeep et al., Sep. 29, 2011, "Discrete Choice Modeling Using Neuro-Response Data"), 20110282231 (Pradeep et al., Nov. 17, 2011, "Mechanisms for Collecting Electroencephalography Data"), 20110282232 (Pradeep et al., Nov. 17, 2011, "Neuro-Response Data Synchronization"), 20120072289 (Pradeep et al., Mar. 22, 2012, "Biometric Aware Content Presentation"), and 20130185144 (Pradeep et al., Jul. 18, 2013, "Systems and Methods for Analyzing Neuro-Response Data and Virtual Reality Environments").

6. Device with Multiple Arms Radially-Forward from Rear and EEG/Brainwave Sensor(s)

Devices in this category hold electromagnetic brain activity sensors in contact with (or proximity to) a person's head using multiple sensor-holding protrusions, fingers, or arms which extend radially forward from a central position at the rear of a person's head. In an example, radially-extending protrusions, fingers, or arms can curve around the head toward the top and sides of the head. To use the colorful language from the previous category, now a figurative starfish (or octopus) is clinging to the back of the person's head. Such devices can be less obtrusive than some of those in the preceding categories, but can still attract attention if worn during the activities of daily life.

Prior art which appears to be within this category includes U.S. Pat. No. 4,770,180 (Schmidt et al., Sep. 13, 1988, "Electroencephalographic Head Set with a Disposable Monitor"), U.S. Pat. No. 4,967,038 (Gevins et al., Oct. 30, 1990, "Dry Electrode Brain Wave Recording System"), U.S. Pat. No. 5,038,782 (Gevins et al., Aug. 13, 1991, "Electrode System for Brain Wave Detection"), and D565,735 (Washbon, Apr. 1, 2008, "Electrode Headset"); and U.S. patent applications 20070225585 (Washbon and Delic, Sep. 27, 2007, "Headset for Electrodes"), 20070238945 (Delic et al., Oct. 11, 2007, "Electrode Headset"), 20090105576 (Do et al., Apr. 23, 2009, "Electrode Conductive Element"), 20120029379 (Sivadas, Feb. 2, 2012, "Mind Strength Trainer"), and 20130046206 (Preminger, Feb. 21, 2013, "System and Method for Neurocognitive Training and/or Neuropsychological Assessment").

7. Device with Multiple Arms Radially-Backward from Front and EEG/Brainwave Sensor(s)

Devices in this category hold electromagnetic brain activity sensors in contact with (or proximity to) a person's head using multiple sensor-holding protrusions, fingers, or arms which extend radially backward from a position on the front of a person's head (such as the forehead). In an example, radially-extending protrusions, fingers, or arms can curve around the head toward the top and sides of the head. Such devices can be obtrusive and attract attention, especially if worn to a showing of the movie "Aliens". Prior art which appears to be within this category includes U.S. patent application 20020188216 (Kayyali et al., Dec. 12, 2002, "Head Mounted Medical Device").

8. Device with Circular Horizontal Loop (e.g. Headband Style) and EEG/Brainwave Sensor(s)

Devices in this category hold electromagnetic brain activity sensors in contact with (or proximity to) a person's head using a sensor-holding member which is configured like a headband, ring, or other generally-circular member which encircles a person's head in (or close to) a horizontal plane when the person is upright. In an example, such a device can span a portion of a person's forehead as it encircles the person's head. Since devices in this category can span a potion of the forehead, such devices can be used with sensors which require contact with (or proximity to) portions of the head which do not have hair. Such devices can be appropriate for wearing while running or doing other types of exercise, but there are still many settings wherein wearing a headband or head-encircling ring is generally not appropriate.

Prior art which appears to be within this category includes U.S. Pat. No. 6,001,065 (Devito, Dec. 14, 1999, "Method and Apparatus for Measuring and Analyzing Physiological Signals for Active or Passive Control of Physical and Virtual Spaces and the Contents Therein"), U.S. Pat. No. 6,171,258 (Karakasoglu et al., Jan. 9, 2001, "Multi-Channel Self-Contained Apparatus and Method for Diagnosis of Sleep Disorders"), U.S. Pat. No. 6,254,536 (Devito, Jul. 3, 2001, "Method and Apparatus for Measuring and Analyzing Physiological Signals for Active or Passive Control of Physical and Virtual Spaces and the Contents Therein"), U.S. Pat. No. 6,811,538 (Westbrook et al., Nov. 2, 2004, "Sleep Apnea Risk Evaluation"), U.S. Pat. No. 7,297,119 (Westbrook et al., Nov. 20, 2007, "Sleep Apnea Risk Evaluation"), and U.S. Pat. No. 7,885,706 (Ludvig et al., Feb. 8, 2011, "System and Device for Seizure Detection").

Prior art which appears to be within this category also includes U.S. patent applications: 20010056225 (DeVito, Dec. 27, 2001, "Method and Apparatus for Measuring and Analyzing Physiological Signals for Active or Passive Control of Physical and Virtual Spaces and the Contents Therein"), 20020165462 (Westbrook et al., Nov. 7, 2002, "Sleep Apnea Risk Evaluation"), 20020188216 (Kayyali et al., Dec. 12, 2002, "Head Mounted Medical Device"), 20040267152 (Pineda, Dec. 20, 2004, "Method and System for Predicting and Preventing Seizures"), 20050027207 (Westbrook et al., Feb. 3, 2005, "Sleep Apnea Risk Evaluation"), and 20070249952 (Rubin et al., Oct. 25, 2007, "Systems and Methods for Sleep Monitoring").

Prior art which appears to be within this category also includes U.S. patent applications: 20080082019 (Ludving et al., Apr. 3, 2008, "System and Device for Seizure Detection"), 20090281446 (Ludvig et al., Nov. 12, 2009, "System and Device for Seizure Detection"), 20100099954 (Dickinson et al., Apr. 22, 2010, "Data-Driven Sleep Coaching System"), 20120150545 (Simon, Jun. 14, 2012, "Brain-Computer Interface Test Battery for the Physiological Assessment of Nervous System Health"), 20130060097 (Rubin, Mar. 7, 2013, "Multi-Modal Sleep System"), 20130127708 (Jung et al., May 23, 2013, "Cell-Phone Based Wireless and Mobile Brain-Machine Interface"), and 20130338446 (Van Vugt et al., Dec. 19, 2013, "Sleep Disturbance Monitoring Apparatus").

9. Device with Top Semicircular Loop (e.g. Headphone Style) and EEG/Brainwave Sensor(s)

Devices in this category hold electromagnetic brain activity sensors in contact with (or proximity to) a person's head using a (semicircular) arcuate member which looks like a set of headphones, hair band, or tiara. In an example, such a device can loop over the top of a person's head, from one side to the other side. In an example, such a device can loop over the top of a person's head from one ear to the other ear. In example, such a device can not only look like a set of headphones, but can actually be a set of headphones, wherein these headphones also include one or more electromagnetic brain activity sensors. Wearing a set of headphones or a hair band is more common (and thus may attract less attention) than wearing most of the devices discussed in preceding categories, but there are still many settings wherein wearing such a device would attract attention and be inappropriate.

Prior art which appears to be within this category includes U.S. Pat. No. 4,697,598 (Bernard et al., Oct. 6, 1987, "Evoked Potential Autorefractometry System"), U.S. Pat. No. 4,709,702 (Sherwin, Dec. 1, 1987, "Electroencephalographic Cap"), U.S. Pat. No. 5,740,812 (Cowan, Apr. 21, 1998, "Apparatus for and Method of Providing Brainwave Biofeedback"), U.S. Pat. No. 6,154,669 (Hunter et al., Nov. 28, 2000, "Headset for EEG Measurements"), U.S. Pat. No. 6,167,298 (Levin, Dec. 26, 2000, "Devices and Methods for Maintaining an Alert State of Consciousness Through Brain Wave Monitoring"), U.S. Pat. No. 7,689,274 (Mullen et al., Mar. 30, 2010, "Brain-Wave Aware Sleep Management"), U.S. Pat. No. 8,271,075 (Chuang et al., Sep. 18, 2012, "Audio Headset with Bio-Signal Sensors"), and U.S. Pat. No. 8,301,218 (Nguyen et al., Oct. 30, 2012, "Contoured Electrode"), U.S. Pat. No. 8,812,075 (Nguyen et al., Aug. 19, 2014, "Contoured Electrode").

Prior art which appears to be within this category also includes U.S. patent applications: 20120029379 (Sivadas, Feb. 2, 2012, "Mind Strength Trainer"), 20120226127 (Asjes et al., Sep. 6, 2012, "Device for Positioning Electrodes on a User's Scalp"), 20130177883 (Barnehama et al., Jul. 11, 2013, "Systems and Methods for Directing Brain Activity"), and 20130310676 (Jung, Nov. 21, 2013, "EEG Hair Band").

10. Device with Rear Semicircular Loop and EEG/Brainwave Sensor(s)

Devices in this category hold electromagnetic brain activity sensors in contact with (or proximity to) a person's head using a (semicircular) arcuate member which loops around the rear portion of a person's head, from one side to the other side. In an example, such a device can loop around the rear portion of a person's head from one ear to the other ear. Such a device can be less obtrusive than many of the devices in preceding categories because it does not span the top of the head or face, but it is not well-suited for use with sensors which require contact with skin without hair. Prior art which appears to be within this category includes U.S. patent application 20140316230 (Denison et al., Oct. 23, 2014, "Methods and Devices for Brain Activity Monitoring Supporting Mental State Development and Training").

11. Device with Frontal Semicircular Loop and EEG/Brainwave Sensor(s)

Devices in this category hold electromagnetic brain activity sensors in contact with (or proximity to) a person's head using a (semicircular) arcuate member which loops around the front of a person's head, from one side to the other side. In an example, such a device can loop around the front of a person's head from one ear to the other ear. In an example, such a device can span a person's forehead. Such a device can be well-suited for use with sensors which require contact with skin without hair, but can be somewhat obtrusive since it spans a portion of a person's face. Prior art which appears to be within this category includes U.S. patent application 20080177197 (Lee et al., Jul. 24, 2008, "Method and Apparatus for Quantitatively Evaluating Mental States Based on Brain Wave Signal Processing System").

12. Device like Eyeglasses or other Eyewear with EEG/Brainwave Sensor(s)

Devices in this category hold electromagnetic brain activity sensors in contact with (or proximity to) a person's head using a sensor-holding member which looks like a pair of eyeglasses, goggles, or other eyewear. In an example, such a device can span from one ear, to the face, across the face (over the bridge of the nose), and then to the other ear. In example, such a device can not only look like a pair of eyeglasses, but can actually be a pair of eyeglasses, wherein these eyeglasses include one or more electromagnetic brain activity sensors. Some of the art in this category predominantly focuses on the optical aspects of a pair of eyeglasses, with only tangential mention of a possible EEG sensor, but such art is included in this category for the sake of completeness. Wearing a pair of eyeglasses is very common and thus attracts less attention than virtually all of the devices discussed in preceding categories. However, conventional eyeglass frames (especially those with straight side pieces) do not contact a person's temple or forehead. Accordingly, conventional eyeglass frame configurations are not ideally-suited for holding one or more electromagnetic brain activity sensors in contact with a person's temple and/or forehead.

Prior art which appears to be within this category includes U.S. Pat. No. 7,344,244 (Goodall et al., Mar. 18, 2008, "Adjustable Lens System with Neural-Based Control"), U.S. Pat. No. 7,390,088 (Goodall et al., Jun. 24, 2008, "Adjustable Lens System with Neural-Based Control"), U.S. Pat. No. 7,486,988 (Goodall et al., Feb. 3, 2009, "Method and System for Adaptive Vision Modification"), U.S. Pat. No. 8,244,342 (Goodall et al., Aug. 14, 2012, "Method and System for Adaptive Vision Modification"), U.S. Pat. No. 8,346,354 (Hyde et al., Jan. 1, 2013, "Determining a Neuromodulation Treatment Regimen in Response to Contactlessly Acquired Information"), U.S. Pat. No. 8,467,133 (Miller, Jun. 18, 2013, "See-Through Display with an Optical Assembly Including a Wedge-Shaped Illumination System"), U.S. Pat. No. 8,472,120 (Border et al., Jun. 25, 2013, "See-Through Near-Eye Display Glasses with a Small Scale Image Source"), U.S. Pat. No. 8,477,425 (Border et al., Jul. 2, 2013, "See-Through Near-Eye Display Glasses Including a Partially Reflective, Partially Transmitting Optical Element"), U.S. Pat. No. 8,482,859 (Border et al., Jul. 9, 2013, "See-Through Near-Eye Display Glasses Wherein Image Light Is Transmitted to and Reflected From an Optically Flat Film"), U.S. Pat. No. 8,488,246 (Border et al., Jul. 16, 2013, "See-Through Near-Eye Display Glasses Including a Curved Polarizing Film in the Image Source, a Partially Reflective, Partially Transmitting Optical Element and an Optically Flat Film"), and U.S. Pat. No. 8,562,540 (Goodall et al., Oct. 22, 2013, "Method and System for Adaptive Vision Modification").

Prior art which appears to be within this category also includes U.S. patent applications: 20060252978 (Vesely et al., Nov. 9, 2006, "Biofeedback Eyewear System"), 20060252979 (Vesely et al., Nov. 9, 2006, "Biofeedback Eyewear System"), 20070010757 (Goodall et al., Jan. 11, 2007, "Method and System for Adaptive Vision Modification"), 20070019279 (Goodall et al., Jan. 25, 2007, "Adjustable Lens System with Neural-Based Control"), 20070106145 (Kim et al., May 10, 2007, "Accessories for Remote Monitoring"), 20080161673 (Goodall et al., Jul. 3, 2008, "Method and System for Adaptive Vision Modification"), 20110028798 (Hyde et al., Feb. 3, 2011, "Electronically Initiating an Administration of a Neuromodulation Treatment Regimen Chosen in Response to Contactlessly Acquired Information"), 20110029038 (Hyde et al., Feb. 3, 2011, "Determining a Neuromodulation Treatment Regimen in Response to Contactlessly Acquired Information"), 20110029044 (Hyde et al., Feb. 3, 2011, "Stimulating a Nervous System Component of a Mammal in Response to Contactlessly Acquired Information"), 20110221656 (Haddick et al., Sep. 15, 2011, "Displayed Content Vision Correction with Electrically Adjustable Lens"), and 20110221669 (Shams et al., Sep. 15, 2011, "Gesture Control in an Augmented Reality Eyepiece").

Prior art which appears to be within this category also includes U.S. patent applications: 20110221672 (Osterhout et al., Sep. 15, 2011, "Hand-Worn Control Device in an Augmented Reality Eyepiece"), 20110222745 (Osterhout et al., Sep. 15, 2011, "Method and Apparatus for Biometric Data Capture"), 20110227820 (Haddick et al., Sep. 22, 2011, "Lock Virtual Keyboard Position in an Augmented Reality Eyepiece"), 20120062445 (Haddick et al., Mar. 15, 2012, "Adjustable Wrap Around Extendable Arm for a Head-Mounted Display"), 20120075168 (Osterhout et al., Mar. 29, 2012, "Eyepiece with Uniformly Illuminated Reflective Display"), 20120150545 (Simon, Jun. 14, 2012, "Brain-Computer Interface Test Battery for the Physiological Assessment of Nervous System Health"), 20120212398 (Border et al., 823/2012, "See-Through Near-Eye Display Glasses Including a Partially Reflective, Partially Transmitting Optical Element"), and 20120212400 (Border et al., Aug. 23, 2012, "See-Through Near-Eye Display Glasses Including a Curved Polarizing Film in the Image Source, a Partially Reflective, Partially Transmitting Optical Element and an Optically Flat Film").

Prior art which appears to be within this category also includes U.S. patent applications: 20120218172 (Border et al., Aug. 30, 2012, "See-Through Near-Eye Display Glasses with a Small Scale Image Source"), 20120218301 (Miller, Aug. 30, 2012, "See-Through Display with an Optical Assembly Including a Wedge-Shaped Illumination System"), 20120235883 (Border et al., Sep. 20, 2012, "See-Through Near-Eye Display Glasses with a Light Transmissive Wedge Shaped Illumination System"), 20120235886 (Border et al., Sep. 20, 2012, "See-Through Near-Eye Display Glasses with a Small Scale Image Source"), 20120235887 (Border et al., Sep. 20, 2012, "See-Through Near-Eye Display Glasses Including a Partially Reflective, Partially Transmitting Optical Element and an Optically Flat Film"), and 20120235900 (Border et al., Sep. 20, 2012, "See-Through Near-Eye Display Glasses with a Fast Response Photochromic Film System for Quick Transition From Dark to Clear").

Prior art which appears to be within this category also includes U.S. patent applications: 20120236030 (Border et al., Sep. 20, 2012, "See-Through Near-Eye Display Glasses Including a Modular Image Source"), 20120242678 (Border et al., Sep. 27, 2012, "See-Through Near-Eye Display Glasses Including an Auto-Brightness Control for the Display Brightness Based on the Brightness in the Environment"), 20120242698 (Haddick et al., Sep. 27, 2012, "See-Through Near-Eye Display Glasses with a Multi-Segment Processor-Controlled Optical Layer"), 20130056010 (Walker et al., Mar. 7, 2013, "Autonomous Positive Airway Pressure System"), 20130127980 (Haddick et al., May 23, 2013, "Video Display Modification Based on Sensor Input for a See-Through Near-to-Eye Display"), and 20130242262 (Lewis, Sep. 19, 2013, "Enhanced Optical and Perceptual Digital Eyewear").

Prior art which appears to be within this category also includes U.S. patent applications: 20130303837 (Berka et al., Nov. 14, 2013, "Systems and Methods for Optimization of Sleep and Post-Sleep Performance"), 20130314303 (Osterhout et al., Nov. 28, 2013, "AR Glasses with User Action Control of and Between Internal and External Applications with Feedback"), 20140023999 (Greder, Jan. 23, 2014, "Detection and Feedback of Information Associated with Executive Function"), 20140267005 (Urbach, Sep. 18, 2014, "Eye Piece for Augmented and Virtual Reality"), 20140267401 (Urbach, Sep. 18, 2014, "Visual Cortex Thought Detector Interface"), 20140347265 (Aimone et al., Nov. 27, 2014, "Wearable Computing Apparatus and Method"), and 20140375545 (Ackerman et al., Dec. 25, 2014, "Adaptive Event Recognition").

SUMMARY OF THE INVENTION

This invention relates to non-invasive Brain Computer Interface (BCI) methods for monitoring and interpreting electromagnetic energy, such as EEG patterns, from a person's brain. The non-invasive BCI methods disclosed herein can enable people with neuromuscular limitations or paralysis to communicate with other people or to control environmental devices via their thought patterns. The non-invasive BCI methods disclosed herein can also enable people to communicate with other people or to control environmental devices via their thought patterns in situations where more conventional modalities (such as touch screen, keyboard, mouse, voice command, or gesture recognition) are not appropriate or not possible.

This invention can be embodied in a Brain Computer Interface (BCI) method which enables a person to control environmental devices, appliances, and/or machines in different action modes based on brain activity patterns which are associated with the same control command across different action modes. In these various examples, one or more action modes can be selected from the group consisting of: speaking a word, phrase, or command; using a touch screen; manually moving a switch, button, dial, or knob on an environmental device, appliance, and/or machine; making a hand gesture; typing a word, phrase, or command; moving a computer mouse; moving one's eyes; and just thinking about controlling an environmental device, appliance, and/or machine.

In an example, a Brain Computer Interface (BCI) system, device, or method can comprise: two or more calibration periods in which a person controls an environmental device in a selected manner by performing actions in two or more different action modes; and a subsequent period in which the person controls the environmental device in the selected manner by performing an action in an action mode which is more convenient, efficient, and/or discreet than either of the first two action modes. In an example, the action mode in the subsequent period can be just thinking about controlling the environmental device in the selected manner. In an example, this invention can be part of the Internet of Thinks (IoT).

In an example, this invention can be embodied in a Brain Computer Interface (BCI) system comprising: a head-worn attachment; at least one electromagnetic brain activity sensor; a microphone; a touch screen; and a data processing unit. In this example, the data processing unit: (a) analyzes electromagnetic brain activity from a first time period within which the person speaks a word or phrase to control an environmental device, appliance, and/or machine in a selected manner; (b) analyzes electromagnetic brain activity from a second period within which the person uses the touch screen to control the environmental device, appliance, and/or machine in the selected manner; (c) identifies a specific pattern shared by electromagnetic brain activity within the first and second periods of time which is associated with controlling the environmental device, appliance, and/or machine in the selected manner; and (d) if the data processing unit detects that specific pattern of electromagnetic brain activity within a third time period, then the data processing unit controls the environmental device, appliance, and/or machine in the selected manner.

INTRODUCTION TO THE FIGURES

DETAILED DESCRIPTION OF THE FIGURES

Figure 1:
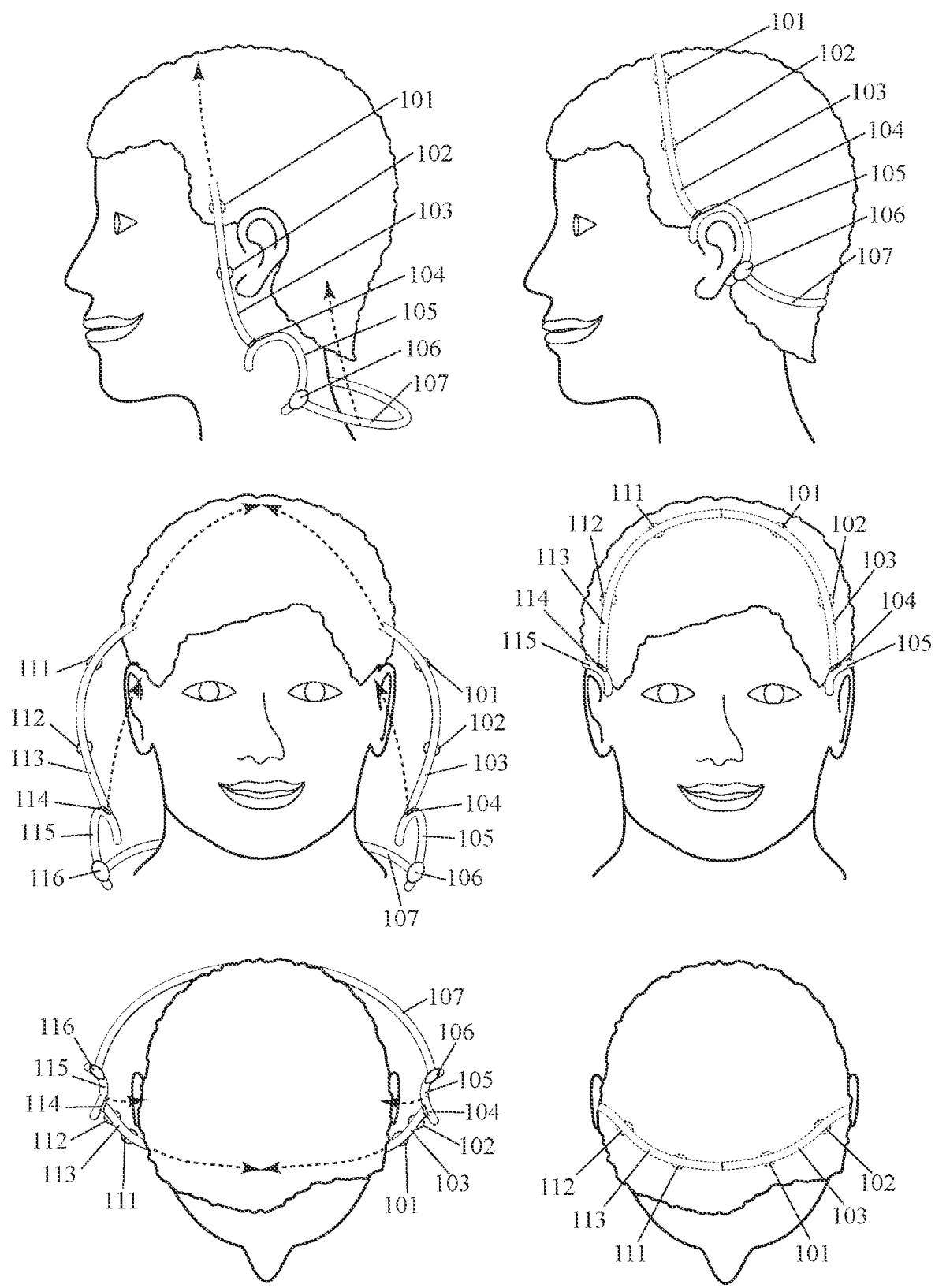
FIG. 1 shows a BCI device with connecting right and left side members which engage a person's hair.

In an example, data concerning a person's brain activity can be collected by one or more electromagnetic energy sensors at one or multiple selected recording sites. In an example, the locations of one or more electromagnetic energy sensors can be selected from the group of EEG placement sites consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In an example, one or more reference places can be selected from the group of sites consisting of A1 and A2.

In an example, collection of data concerning brain activity can comprise measuring electromagnetic data concerning impedance, voltage difference, and/or energy transfer between two sites on a person's head—a selected recording site and a reference site. In an example, electromagnetic brain activity data can be collected by an electromagnetic energy sensor at a selected recording place. In an example, electromagnetic brain activity data from a selected recording place (relative to a reference place) can be called a "channel" In an example, electromagnetic brain activity data from multiple recording places can be called a "montage." In an example, brain activity data can be recorded at a rate in the range of 100 to 300 samples per second.

In an example, a statistical method can be used to identify specific patterns in a person's electromagnetic brain activity and/or specific changes in a person's electromagnetic brain activity. In an example, data from one or more electromagnetic energy sensors can be filtered to remove artifacts before the application of a statistical method. In an example, a filter can be used to remove electromagnetic signals from eye blinks, eye flutters, or other eye movements before the application of a statistical method. In an example, a notch filter can be used as well to remove 60 Hz artifacts caused by AC electrical current. In various examples, one or more filters can be selected from the group consisting of: a high-pass filter, a band-pass filter, a loss-pass filter, an electromyographic activity filter, a 0.5-1 Hz filter, and a 35-70 Hz filter.

In an example, a pattern and/or change in electromagnetic brain activity can be a one-time pattern. In another example, a pattern of electromagnetic brain activity can repeat over time in a rhythmic manner. In an example, a primary statistical method can analyze repeating electromagnetic patterns by analyzing their frequency of repetition, their frequency band or range of repetition, their recurring amplitude, their wave phase, and/or their waveform. In an example repeating patterns and/or waveforms can be analyzed using Fourier Transform methods.

In an example, a primary statistical method for identifying patterns and/or changes in electromagnetic brain activity can comprise finding the mean or average value of data from one or more brain activity channels during a period of time. In an example, a statistical method can comprise identifying a significant change in the mean or average value of data from one or more brain activity channels. In an example, a statistical method can comprise finding the median value of data from one or more brain activity channels during a period of time. In an example, a statistical method can comprise identifying a significant change in the median value of data from one or more brain activity channels. In an example, a statistical method can comprise identifying significant changes in the relative mean or median data values among multiple brain activity channels. In an example, a statistical method can comprise identifying significant changes in mean data values from a first set of sensor locations relative to mean data values from a second set of sensor locations. In an example, a statistical method can comprise identifying significant changes in mean data recorded from a first region of the brain relative to mean data recorded from a second region of the brain.

In an example, a primary statistical method for identifying patterns and/or changes in electromagnetic brain activity can comprise finding the minimum or maximum value of data from one or more brain activity channels during a period of time. In an example, a statistical method can comprise identifying a significant change in the minimum or maximum value of data from one or more brain activity channels. In an example, a statistical method can comprise identifying significant changes in the relative minimum or maximum data values among multiple brain activity channels. In an example, a statistical method can comprise identifying significant changes in minimum or maximum data values from a first set of sensor locations relative to minimum or maximum data values from a second set of sensor locations. In an example, a statistical method can comprise identifying significant changes in minimum or maximum data values recorded from a first region of the brain relative to minimum or maximum data values recorded from a second region of the brain.

In an example, a primary statistical method for identifying patterns and/or changes in electromagnetic brain activity can comprise finding the variance or the standard deviation of data from one or more brain activity channels during a period of time. In an example, a statistical method can comprise identifying a significant change in the variance or the standard deviation of data from one or more brain activity channels. In an example, a statistical method can comprise identifying significant changes in the covariation and/or correlation among data from multiple brain activity channels. In an example, a statistical method can comprise identifying significant changes in the covariation or correlation between data from a first set of sensor locations relative and data from a second set of sensor locations. In an example, a statistical method can comprise identifying significant changes in the covariation or correlation of data values recorded from a first region of the brain and a second region of the brain.

In an example, a primary statistical method for identifying patterns and/or changes in electromagnetic brain activity can comprise finding the amplitude of waveform data from one or more channels during a period of time. In an example, a statistical method can comprise identifying a significant change in the amplitude of waveform data from one or more channels. In an example, a statistical method can comprise identifying significant changes in the relative wave amplitudes from one or more channels. In an example, a statistical method can comprise identifying significant changes in the amplitude of electromagnetic signals recorded from a first region of the brain relative to the amplitude of electromagnetic signals recorded from a second region of the brain.

In an example, a primary statistical method for identifying patterns and/or changes in electromagnetic brain activity can comprise finding the power of waveform brain activity data from one or more channels during a period of time. In an example, a statistical method can comprise identifying a significant change in the power of waveform data from one or more channels. In an example, a statistical method can comprise identifying significant changes in the relative power levels of one or more channels. In an example, a statistical method can comprise identifying significant changes in the power of electromagnetic signals recorded from a first region of the brain relative to the power of electromagnetic signals recorded from a second region of the brain.

In an example, a primary statistical method for identifying patterns and/or changes in electromagnetic brain activity can comprise finding a frequency or a frequency band of waveform and/or rhythmic brain activity data from one or more channels which repeats over time. In an example, Fourier Transform methods can be used to find a frequency or a frequency band of waveform and/or rhythmic data which repeats over time. In an example, a statistical method can comprise decomposing a complex waveform into a combination of simpler waveforms which each repeat at a different frequency or within a different frequency band. In an example, Fourier Transform methods can be used to decomposing a complex waveform into a combination of simpler waveforms which each repeat at a different frequency or within a different frequency band.

In an example, a primary statistical method for identifying patterns and/or changes in electromagnetic brain activity can comprise identifying significant changes in the amplitude, power level, phase, frequency, covariation, entropy, and/or oscillation of waveform data from one or more channels. In an example, a statistical method can comprise identifying significant changes in the amplitude, power level, phase, frequency, covariation, entropy, and/or oscillation of waveform data within a selected frequency band. In an example, a statistical method can comprise identifying significant changes in the relative amplitudes, power levels, phases, frequencies, covariations, entropies, and/or oscillations of waveform data among different frequency bands. In various examples, these significant changes can be identified using Fourier Transform methods.

In an example, brainwaves or other rhythmic, cyclical, and/or repeating electromagnetic signals associated with brain activity can be measured and analyzed using one or more clinical frequency bands. In an example, complex repeating waveform patterns can be decomposed and identified as a combination of multiple, simpler repeating wave patterns, wherein each simpler wave pattern repeats within a selected clinical frequency band. In an example, brainwaves can be decomposed and analyzed using Fourier Transformation methods. In an example, brainwaves can be measured and analyzed using a subset and/or combination of five clinical frequency bands: Delta, Theta, Alpha, Beta, and Gamma. In an example, a method can analyze changes in brainwaves in a single frequency band, changes in brainwaves in multiple frequency bands, or changes in brainwaves in a first frequency band relative to those in a second frequency band.

In an example, Delta brainwaves can be measured and analyzed within a frequency band of 1 to 4 Hz. In various examples, Delta brainwaves or other rhythmic, cyclical, and/or repeating electromagnetic signals associated with brain activity can be measured and analyzed within a frequency band selected from the group consisting of: 0.5-3.5 Hz, 0.5-4 Hz, 1-3 Hz, 1-4 Hz, and 2-4 Hz. In an example, a method can track a decrease or increase in the relative power of brainwaves in the Delta band. In an example, a method can track a frequency shift within the Delta frequency band. In an example, a method can track a change in wave shape for brainwaves in the Delta frequency band. In an example, a method can track a change in which brain regions originate or modify brainwaves within the Delta frequency band. In an example, a method can track a change in brainwave activity within the Delta band from the anterior vs. posterior areas of a person's brain. In an example, a method can track a change in brainwave activity within the Delta band for a particular brain lobe or organelle. In an example, a method can track a change in brainwave activity within the Delta band as measured from a specific sensor site, a specific sensor channel, and/or a specific montage of channels.

In an example, Theta brainwaves can be measured and analyzed within a frequency band of 4 to 8 Hz. In various examples, Theta brainwaves or other rhythmic, cyclical, and/or repeating electromagnetic signals associated with brain activity can be measured and analyzed within a frequency band selected from the group consisting of: 3.5-7 Hz, 3-7 Hz, 4-7 Hz, 4-7.5 Hz, 4-8 Hz, and 5-7 Hz. In an example, a method can track changes in the power of brainwaves in the Theta band. In an example, a method can track a frequency shift within the Theta band. In an example, a method can track changes in wave shape for brainwaves in the Theta band. In an example, a method can track a change in which brain regions originate or modify brainwaves within the Theta band. In an example, a method can track a change in brainwave activity within the Theta band as measured from a specific sensor site, a specific sensor channel, and/or a specific montage of channels.

In an example, Alpha brainwaves can be measured and analyzed within a frequency band of 7 to 14 Hz. In various examples, Alpha brainwaves or other rhythmic, cyclical, and/or repeating electromagnetic signals associated with brain activity can be measured and analyzed within a frequency band selected from the group consisting of: 7-13 Hz, 7-14 Hz, 8-12 Hz, 8-13 Hz, 7-11 Hz, 8-10 Hz, and 8-10 Hz. In an example, a method can track an increase or decrease in the relative power of brainwaves in the Alpha band. In an example, a method can track a downward or upward shift in the frequency of brainwaves within the Alpha band. In an example, a method can track a change in wave shape for brainwaves in the Alpha frequency band. In an example, a method can track a change in which brain regions originate or modify brainwaves within the Alpha frequency band. In an example, a method can track a change in brainwave activity within the Alpha band on one side of a person's brain relative to the other side. In an example, a method can track a change in brainwave activity within the Alpha band in a particular brain lobe or organelle. In an example, a method can track a change in brainwave activity within the Alpha band as measured from a specific sensor site, a specific sensor channel, and/or a specific montage of channels.

In an example, Beta brainwaves can be measured and analyzed within a frequency band of 12 to 30 Hz. In various examples, Beta brainwaves or other rhythmic, cyclical, and/or repeating electromagnetic signals associated with brain activity can be measured and analyzed within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. In an example, specific patterns or trends in brainwaves in the Beta frequency band can be statistically identified.

In an example, Gamma brainwaves can be measured and analyzed within a frequency band of 30 to 100 Hz. In various examples, Gamma brainwaves or other rhythmic, cyclical, and/or repeating electromagnetic signals associated with brain activity can be measured and analyzed within a frequency band selected from the group consisting of: 30-100 Hz, 35-100 Hz, 40-100 Hz, and greater than 30 Hz. In an example, specific patterns or trends in brainwaves in the Gamma frequency band can be statistically identified. In an example, a person can be identified as having the "World's Best Gamma" and receive an appropriately-labeled coffee mug.

In an example, a primary statistical method can employ multivariate analysis of electromagnetic brainwave activity in the Delta, Theta, and Alpha frequency bands to identify patterns. In an example, a primary statistical method can comprise calculating an arithmetic function, or a change in an arithmetic function, of the different power levels in multiple frequency bands. In an example, a primary statistical method can comprise a difference, or a change in a difference, between power levels in different frequency bands. In an example, a primary statistical method can comprise a ratio, or a change in a ratio, of power levels in different frequency bands. In an example, a primary statistical method can comprise a sum, or a change in a sum, of power levels in different frequency bands. In an example, a primary statistical method can comprise a product, or a change in a product, of power levels in different frequency bands.

In various examples, specific patterns of electromagnetic brain activity can be analyzed and identified using one or more methods selected from the group consisting of: ANOVA or MANOVA; artificial neural network; auto-regression; Bonferroni analysis; centroid analysis; chi-squared analysis; cluster analysis and grouping; decision tree or random forest analysis; Discrete Fourier transform (DFT), Fast Fourier Transform (FFT), or other Fourier Transform methods; factor analysis; feature vector analysis; fuzzy logic model; Gaussian model; hidden Markov model, input-output hidden Markov model, or other Markov model; inter-band mean; inter-band ratio; inter-channel mean; inter-channel ratio; inter-montage mean; inter-montage ratio; Kalman filter; kernel estimation; linear discriminant analysis; linear transform; logit model; machine learning; mean power; mean; median; multi-band covariance analysis; multi-channel covariance analysis; multivariate linear regression or multivariate least squares estimation; multivariate logit or other multivariate parametric classifiers; naïve Bayes classifier, trained Bayes classifier, dynamic Bayesian network, or other Bayesian methods; non-linear programming; pattern recognition; power spectral density or other power spectrum analysis; principal components analysis; probit model; support vector machine; time-series model; T-test; variance, covariance, or correlation; waveform identification; multi-resolution wavelet analysis or other wavelet analysis; whole band power; support vector machine; and Z-scores or other data normalization method.

In an example, a power source can be a rechargeable battery. In an example, a power source can be selected from the group consisting of: a rechargeable or replaceable battery; an energy harvesting member which harvests, transduces, or generates energy from body motion or kinetic energy, body thermal energy, or body biochemical energy; an energy harvesting member which harvests, transduces, or generates energy from ambient light energy or ambient electromagnetic energy.

In an example, a data processing unit can process data from one or more electromagnetic energy sensors. In an example a data processing unit can be a microchip, circuit board, CPU, and/or miniature computer. In an example, a data transmitter and/or receiver can be a wireless data transmitter and/or receiver. In an example, data transmitter and/or receiver can be in wireless communication with a remote computer, a handheld electronic device, a separate wearable device, a separate array of wearable sensors, a communication network tower, a satellite, a home control system, and/or an implantable medical device.

FIGS. 1 through 8 show examples of how this invention can be embodied in a hair-engaging mobile brain activity monitor comprising: (1) an arcuate frame which is configured to be worn on a person's head, wherein this arcuate frame further comprises: (1a) a right ear loop which is configured to curve around the person's right ear; (1b) a left ear loop which is configured to curve around the person's left ear; (1c) a posterior loop which is connected to the right ear loop and the left ear loop, where this posterior loop is configured to curve around a posterior portion of a person's head; (1d) a right upward-extending member which is configured to extend upward toward the top of the person's head from the right ear loop and/or from the posterior loop, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and (1e) a left upward-extending member which is configured to extend upward toward the top of the person's head from the left ear loop and/or from the posterior loop, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; (2) one or more electromagnetic energy sensors which collect data concerning electromagnetic brain activity; (3) a power source; (4) a data processing unit; and (5) a data transmitter and/or receiver.

FIG. 1 shows an example of how this invention can be embodied in a hair-engaging mobile brain activity monitor. The top third of FIG. 1 (two sequential pictures of the side of a person's head) shows this monitor from a perspective looking at the side of a person's head. The middle third of FIG. 1 (two sequential pictures of the front of a person's head) shows this monitor from a perspective looking at the front of a person's head. The bottom third of FIG. 1 (two sequential pictures of the top of a person's head) shows this monitor from a perspective looking down at the top of a person's head. The left side of FIG. 1 (three pictures from three different perspectives) shows this monitor at a first point in time, in a first configuration, before it is worn on the head and engages the person's hair. The right side of FIG. 1 (three pictures from three different perspectives) shows this same monitor at a second point in time, in a second configuration, when it is worn on the head and engages the person's hair.

The top third of FIG. 1 shows the hair-engaging mobile brain activity monitor from a left side perspective. As seen in this top third of FIG. 1, this brain activity monitor comprises: an arcuate frame which is configured to be worn on a person's head, wherein this arcuate frame further comprises: a left ear loop 105 which is configured to curve around the person's left ear; a posterior loop 107 which is connected to the left ear loop 105, where this posterior loop 107 is configured to curve around a posterior portion of a person's head; and a left upward-extending member 103 which is configured to extend upward toward the top of the person's head from the left ear loop 105, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 101 and 102, which collect data concerning electromagnetic brain activity; and a left-side housing 106 which contains a power source, a data processing unit, and a data transmitter and/or receiver. This example further comprises a left-side hinge 104 between left ear loop 105 and left upward-extending member 103.

The left side of the top third of FIG. 1 shows this monitor at first point in time, in the first configuration, wherein posterior loop 107 has been flexed outward, left ear loop 105 is not yet worn around the left ear, and only the upper tip of left upward-extending member 103 has been inserted into the person's hair. In these examples, the portion of an upward-extending member which has been inserted into a person's hair, engaging the hair strands and/or sliding upwards under a layer of hair, is represented by dotted lines to show that it is partially obscured from view. On the left side of the top third of FIG. 1, only the upper tip of left upward-extending member 103 is shown with dotted lines since only the tip has been inserted into the person's hair at this time, in the first configuration.

The right side of the top third of FIG. 1 shows this monitor at a second point in time, in the second configuration, wherein posterior loop 107 has flexed inward, left ear loop 105 is now worn around a portion of the left ear, and most of the upward-extending member 103 has been upwardly inserted into the person's hair, engaging the hair strands and/or sliding upwards under a layer of hair. This is why most of upward-extending member 103 is shown with dotted lines on the right side at this second point in time, in the second configuration.

The middle third of FIG. 1 shows this same hair-engaging mobile brain activity monitor from a frontal face perspective. This perspective shows right-side components of the monitor as well as left-side components. Right-side components shown for the first time in this perspective include: a right ear loop 115 which is configured to curve around the person's right ear; a right upward-extending member 113 which is configured to extend upward toward the top of the person's head from the right ear loop 115, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more right-side electromagnetic energy sensors, 111 and 112, which collect data concerning electromagnetic brain activity; and a right-side housing 116 which contains a power source, a data processing unit, and a data transmitter and/or receiver. This example further comprises a right-side hinge 114 between right ear loop 115 and right upward-extending member 113.

The left side of the middle third of FIG. 1 again shows this monitor at first point in time, in the first configuration, but this time from a frontal face perspective. From this perspective, it can be clearly seen that posterior loop 107 has been flexed outward, that right and left ear loops 115 and 105 are not yet worn around the ears, and that only the upper tips of right and left upward-extending members 113 and 103 have been inserted into the person's hair. The right side of the middle third of FIG. 1 shows this monitor at a second point in time, in the second configuration. From this perspective, it can be clearly seen that posterior loop 107 has flexed inward, that right and left ear loops 115 and 105 are now worn around the ears, and that most of right and left upward-extending members 113 and 103 have now been inserted into the person's hair. Also, in this example, the upper tips of right and left upward-extending members 113 and 103 have been connected or attached to each other in the second configuration.

The bottom third of FIG. 1 shows this same hair-engaging mobile brain activity monitor from a top-down perspective. The left side of the bottom third of FIG. 1 again shows this monitor at first point in time, in the first configuration. From this perspective, it can be clearly seen that posterior loop 107 has been flexed outward, that right and left ear loops 115 and 105 are not yet worn around the ears, and that only the upper tips of right and left upward-extending members 113 and 103 have been inserted into the person's hair. The right side of the bottom third of FIG. 1 shows this monitor at a second point in time, in the second configuration. From this perspective, it can be clearly seen that posterior loop 107 has flexed inward, that right and left ear loops 115 and 105 are now worn around the ears, and that most of right and left upward-extending members 113 and 103 have now been inserted into the person's hair. Also, in this example, the upper tips of right and left upward-extending members 113 and 103 have been connected or attached to each other in the second configuration. Relevant example and design variations discussed elsewhere in this disclosure can also be applied to the example shown here in FIG. 1.

Figure 2:
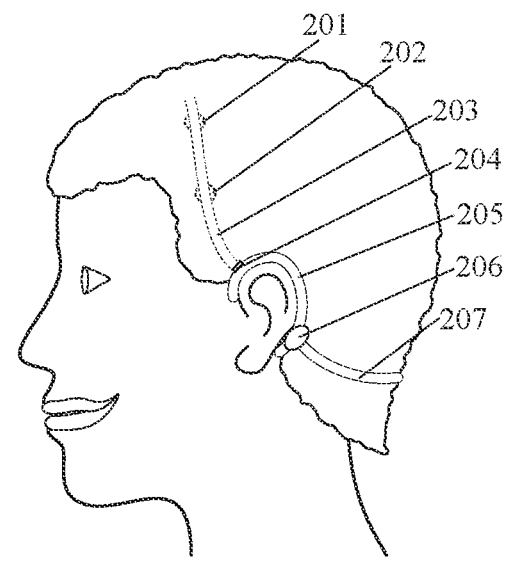
FIG. 2 shows a BCI device with non-connecting right and left side members which engage a person's hair.
Figure 2:
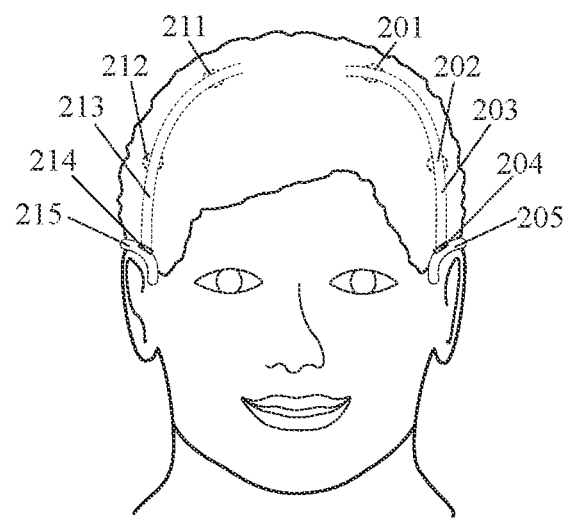
Figure 2:
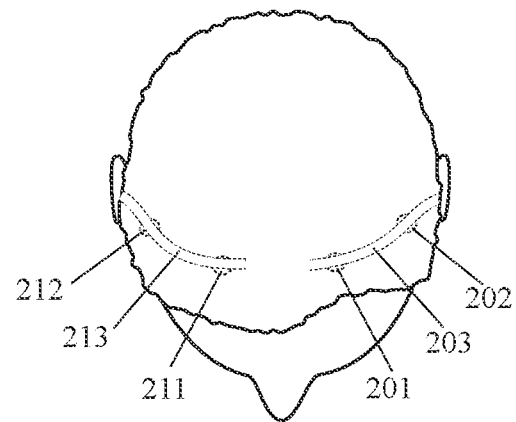

FIG. 2 shows another example of how this invention can be embodied in a hair-engaging mobile brain activity monitor. The monitor shown in this example is similar to the one shown in FIG. 1 except that the upper tips of the right and left upward-extending members are not connected to each other in the second configuration. Another difference between FIG. 2 and FIG. 1 is that FIG. 2 only shows the monitor in the second configuration. Movement of the device from the first configuration to the second configuration occurs in a manner similar to the device shown in FIG. 1, so these sequential perspectives are not shown again in FIG. 2. The top third of FIG. 2 shows this monitor looking at the side of a person's head. The middle third of FIG. 2 shows this monitor looking at the front of a person's head. The bottom third of FIG. 2 shows this monitor looking down at the top of a person's head.

As shown in the top third of FIG. 2, this brain activity monitor comprises: an arcuate frame which is configured to be worn on a person's head, wherein this arcuate frame further comprises: a left ear loop 205 which is configured to curve around the person's left ear; a posterior loop 207 which is connected to the left ear loop 205, where this posterior loop 207 is configured to curve around a posterior portion of a person's head; and a left upward-extending member 203 which is configured to extend upward toward the top of the person's head from the left ear loop 205, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 201 and 202, which collect data concerning electromagnetic brain activity; and a left-side housing 206 which contains a power source, a data processing unit, and a data transmitter and/or receiver. This example further comprises a left-side hinge 204 between left ear loop 205 and left upward-extending member 203.

The middle third of FIG. 2 shows this same hair-engaging mobile brain activity monitor from a frontal face perspective. This perspective shows right-side components of the monitor as well as left-side components. Right-side components shown for the first time in this perspective include: a right ear loop 215 which is configured to curve around the person's right ear; a right upward-extending member 213 which is configured to extend upward toward the top of the person's head from the right ear loop 215, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 211 and 212, which collect data concerning electromagnetic brain activity. This example further comprises a right-side hinge 214 between right ear loop 215 and right upward-extending member 213. In this example, the upper tips of right and left upward-extending members 213 and 203 are not connected or attached to each other, even in the second configuration.

The bottom third of FIG. 2 shows this same hair-engaging mobile brain activity monitor from a top-down perspective. In this example, the upper tips of right and left upward-extending members 213 and 203 are not connected or attached to each other, even in the second configuration. Relevant example and design variations discussed elsewhere in this disclosure can also be applied to the example shown here in FIG. 2.

Figure 3:
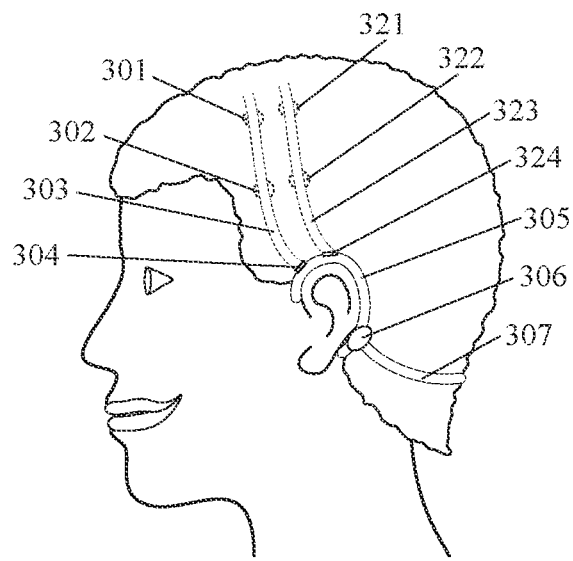
FIG. 3 shows a BCI device with dual right and dual left side members which engage a person's hair.
Figure 3:
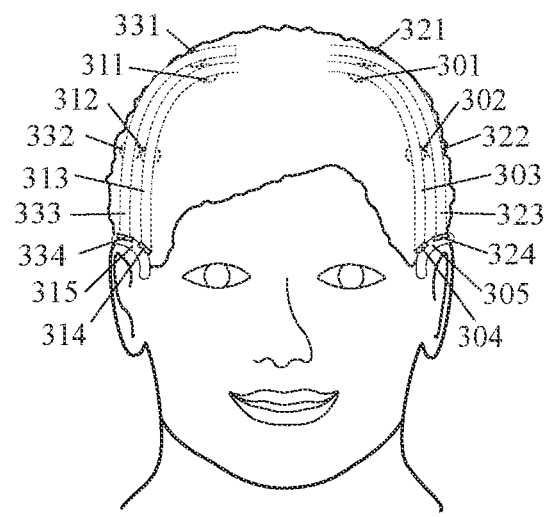
Figure 3:
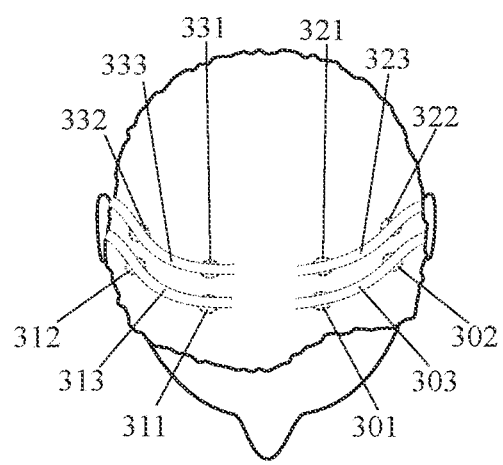

FIG. 3 shows another example of how this invention can be embodied in a hair-engaging mobile brain activity monitor. The monitor shown in this example is similar to the one shown in FIG. 2 except that there are two, generally parallel, upward-extending members on each side of the person's head. The top third of FIG. 3 shows this monitor looking at the side of a person's head. The middle third of FIG. 3 shows this monitor looking at the front of a person's head. The bottom third of FIG. 3 shows this monitor looking down at the top of a person's head.

As shown in the top third of FIG. 3, this brain activity monitor comprises: an arcuate frame which is configured to be worn on a person's head, wherein this arcuate frame further comprises: a left ear loop 305 which is configured to curve around the person's left ear; a posterior loop 307 which is connected to the left ear loop 305, where this posterior loop 307 is configured to curve around a posterior portion of a person's head; a first left upward-extending member 303 which is configured to extend upward toward the top of the person's head from the left ear loop 305, wherein this first left upward-extending member has a first configuration in which its upper-most portion is a first distance from the top of the person's head, wherein this first left upward-extending member has a second configuration in which its upper-most portion is a second distance from the top of the person's head, wherein the second distance is less than the first distance, and wherein the first left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; a second left upward-extending member 323 which is configured to extend upward toward the top of the person's head from the left ear loop 305, wherein this second left upward-extending member has a first configuration in which its upper-most portion is a first distance from the top of the person's head, wherein this second left upward-extending member has a second configuration in which its upper-most portion is a second distance from the top of the person's head, wherein the second distance is less than the first distance, and wherein the second left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 301, 302, 321, and 322, which collect data concerning electromagnetic brain activity; and a left-side housing 306 which contains a power source, a data processing unit, and a data transmitter and/or receiver. This example further comprises a first left-side hinge 304 between left ear loop 305 and first left upward-extending member 303 and a second left-side hinge 324 between left ear loop 305 and second left upward-extending member 323.

The middle third of FIG. 3 shows this same hair-engaging mobile brain activity monitor from a frontal face perspective. This perspective shows right-side components of the monitor as well as left-side components. Right-side components shown for the first time in this perspective include: a right ear loop 315 which is configured to curve around the person's right ear; a first right upward-extending member 313 which is configured to extend upward toward the top of the person's head from the right ear loop 315, wherein this first right upward-extending member has a first configuration in which its upper-most portion is a first distance from the top of the person's head, wherein this first right upward-extending member has a second configuration in which its upper-most portion is a second distance from the top of the person's head, wherein the second distance is less than the first distance, and wherein the first right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; a second right upward-extending member 333 which is configured to extend upward toward the top of the person's head from the right ear loop 315, wherein this second right upward-extending member has a second configuration in which its upper-most portion is a second distance from the top of the person's head, wherein this second right upward-extending member has a second configuration in which its upper-most portion is a second distance from the top of the person's head, wherein the second distance is less than the second distance, and wherein the second right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 311, 312, 331, and 332, which collect data concerning electromagnetic brain activity. This example further comprises a first right-side hinge 314 between right ear loop 315 and first right upward-extending member 313 and a second right-side hinge 334 between right ear loop 315 and second right upward-extending member 333. In this example, the upper tips of right and left upward-extending members are not connected or attached to each other, even in the second configuration.

The bottom third of FIG. 3 shows this same hair-engaging mobile brain activity monitor from a top-down perspective. In this example, the upper tips of right and left upward-extending members are not connected or attached to each other, even in the second configuration. Relevant example and design variations discussed elsewhere in this disclosure can also be applied to the example shown here in FIG. 3.

Figure 4:
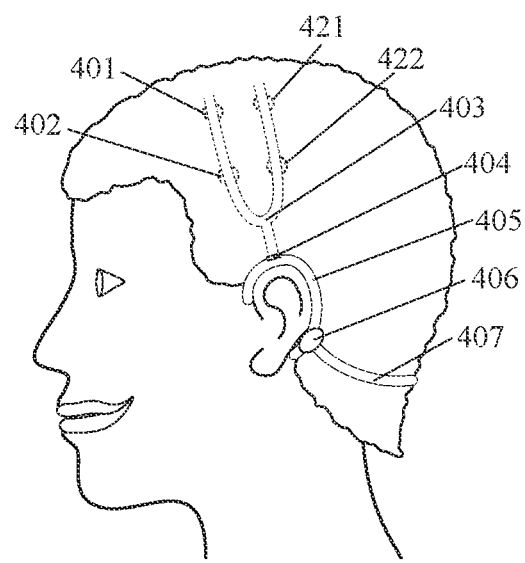
FIG. 4 shows a BCI device with Y-shaped right and left side members which engage a person's hair.
Figure 4:
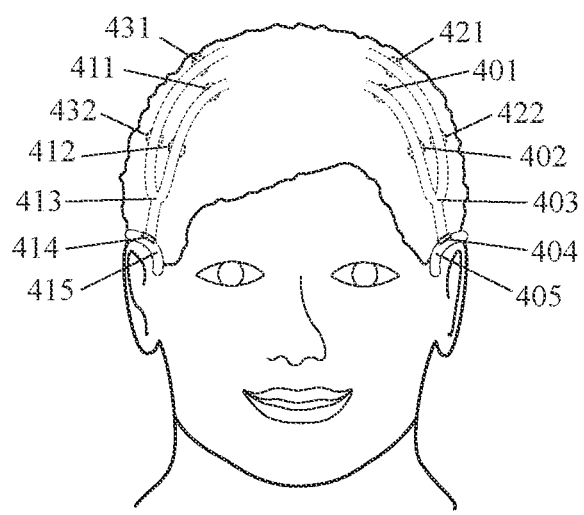
Figure 4:
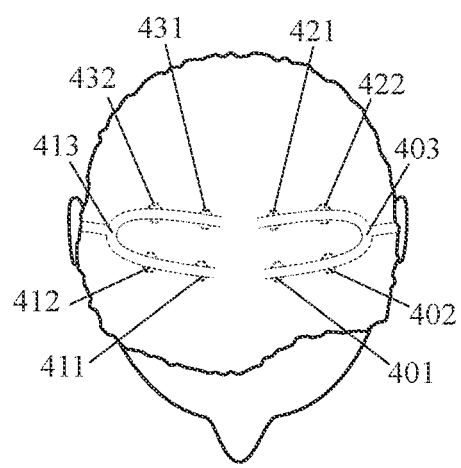

FIG. 4 shows another example of how this invention can be embodied in a hair-engaging mobile brain activity monitor. The monitor shown in this example is similar to the one shown in FIG. 2 except that the upper portion of an upward-extending member bifurcates (looking similar to a capital letter "Y"). The top third of FIG. 4 shows this monitor looking at the side of a person's head. The middle third of FIG. 4 shows this monitor looking at the front of a person's head. The bottom third of FIG. 4 shows this monitor looking down at the top of a person's head.

As shown in the top third of FIG. 4, this brain activity monitor comprises: an arcuate frame which is configured to be worn on a person's head, wherein this arcuate frame further comprises: a left ear loop 405 which is configured to curve around the person's left ear; a posterior loop 407 which is connected to the left ear loop 405, where this posterior loop 407 is configured to curve around a posterior portion of a person's head; a bifurcating left upward-extending member 403 which is configured to extend upward toward the top of the person's head from the left ear loop 405, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 401, 402, 421, and 422, which collect data concerning electromagnetic brain activity; and a left-side housing 406 which contains a power source, a data processing unit, and a data transmitter and/or receiver. This example further comprises a left-side hinge 404 between left ear loop 405 and left upward-extending member 403.

The middle third of FIG. 4 shows this same hair-engaging mobile brain activity monitor from a frontal face perspective. This perspective shows right-side components of the monitor as well as left-side components. Right-side components shown for the first time in this perspective include: a right ear loop 415 which is configured to curve around the person's right ear; a bifurcating right upward-extending member 413 which is configured to extend upward toward the top of the person's head from the right ear loop 415, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 411, 412, 431, and 432, which collect data concerning electromagnetic brain activity. This example further comprises a right-side hinge 414 between right ear loop 415 and right upward-extending member 413. In this example, the upper tips of right and left upward-extending members are not connected or attached to each other, even in the second configuration.

The bottom third of FIG. 4 shows this same hair-engaging mobile brain activity monitor from a top-down perspective. In this example, the upper tips of right and left upward-extending members are not connected or attached to each other, even in the second configuration. Relevant example and design variations discussed elsewhere in this disclosure can also be applied to the example shown here in FIG. 4.

Figure 5:
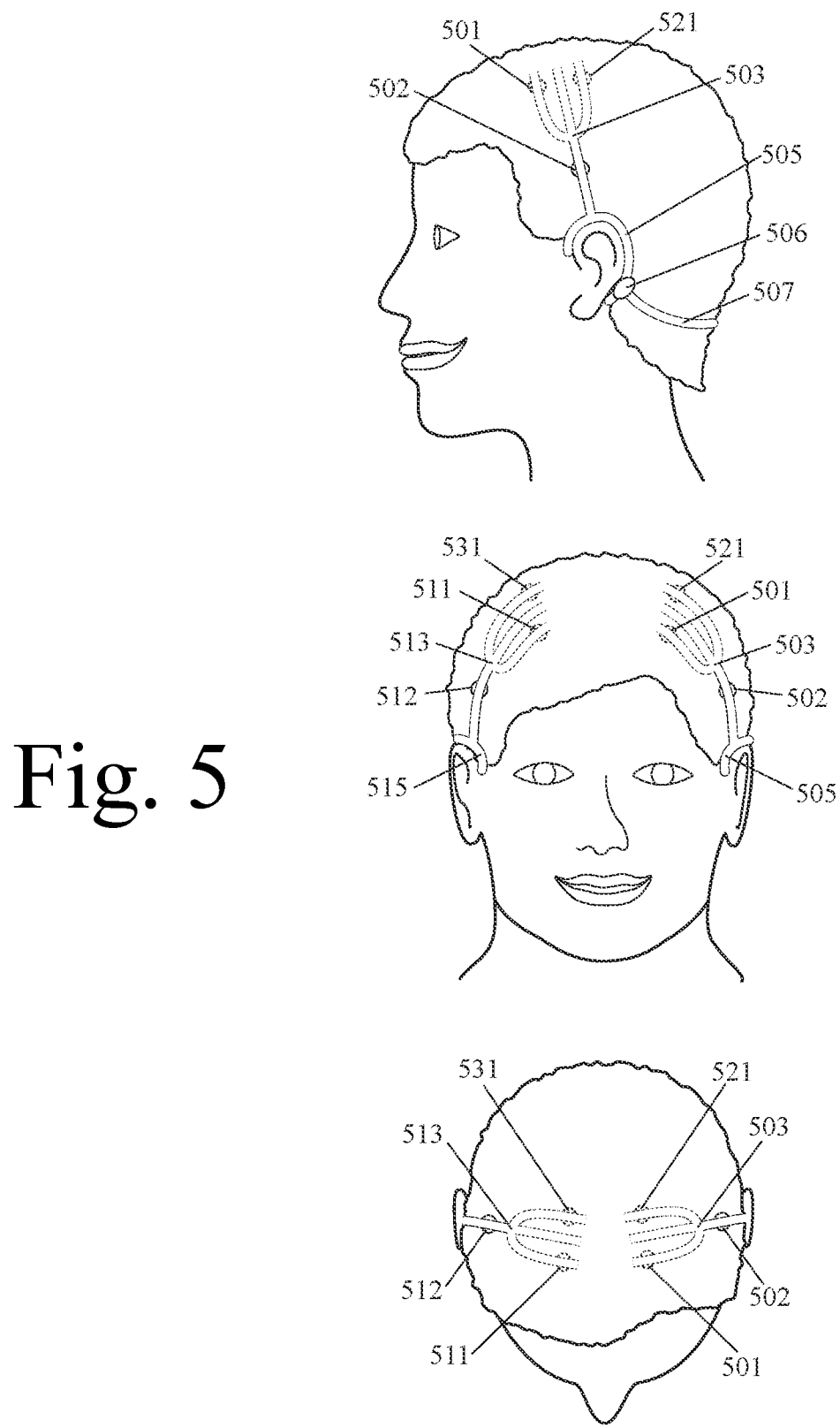
FIG. 5 shows a BCI device with trident-shaped right and left side members which engage a person's hair.

FIG. 5 shows another example of how this invention can be embodied in a hair-engaging mobile brain activity monitor. The monitor shown in this example is similar to the one shown in FIG. 2 except that the upper portion of an upward-extending member trifurcates (looking similar to a trident). The top third of FIG. 5 shows this monitor looking at the side of a person's head. The middle third of FIG. 5 shows this monitor looking at the front of a person's head. The bottom third of FIG. 5 shows this monitor looking down at the top of a person's head.

As shown in the top third of FIG. 5, this brain activity monitor comprises: an arcuate frame which is configured to be worn on a person's head, wherein this arcuate frame further comprises: a left ear loop 505 which is configured to curve around the person's left ear; a posterior loop 507 which is connected to the left ear loop 505, where this posterior loop 507 is configured to curve around a posterior portion of a person's head; a trifurcating left upward-extending member 503 which is configured to extend upward toward the top of the person's head from the left ear loop 505, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 501, 502, and 521, which collect data concerning electromagnetic brain activity; and a left-side housing 506 which contains a power source, a data processing unit, and a data transmitter and/or receiver.

The middle third of FIG. 5 shows this same hair-engaging mobile brain activity monitor from a frontal face perspective. This perspective shows right-side components of the monitor as well as left-side components. Right-side components shown for the first time in this perspective include: a right ear loop 515 which is configured to curve around the person's right ear; a trifurcating right upward-extending member 513 which is configured to extend upward toward the top of the person's head from the right ear loop 515, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 511, 512, and 531, which collect data concerning electromagnetic brain activity. In this example, the upper tips of right and left upward-extending members are not connected or attached to each other, even in the second configuration.

The bottom third of FIG. 5 shows this same hair-engaging mobile brain activity monitor from a top-down perspective. In this example, the upper tips of right and left upward-extending members are not connected or attached to each other, even in the second configuration. Relevant example and design variations discussed elsewhere in this disclosure can also be applied to the example shown here in FIG. 5.

Figure 6:
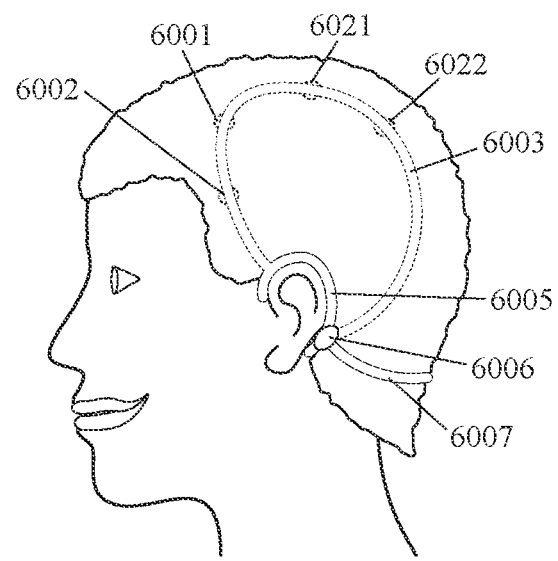
FIG. 6 shows a BCI device with non-connecting right and left side loops which engage a person's hair.
Figure 6:
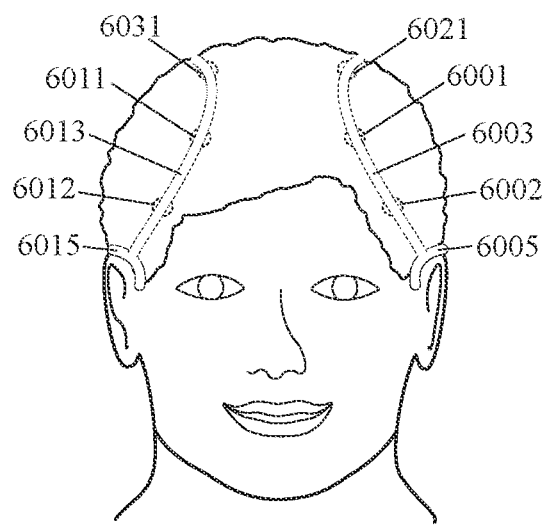
Figure 6:
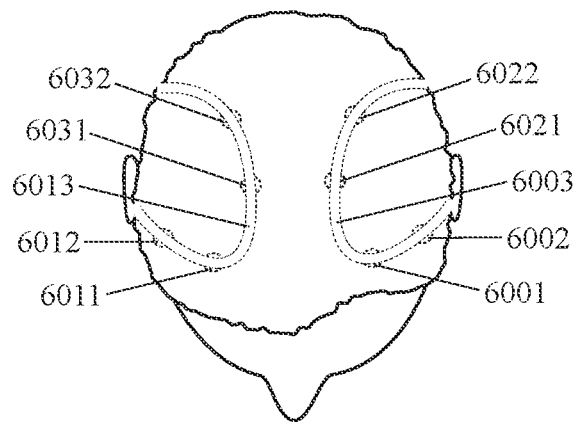

FIG. 6 shows another example of how this invention can be embodied in a hair-engaging mobile brain activity monitor. The monitor shown in this example is similar to the one shown in FIG. 2 except that the upward-extending member is a loop. The top third of FIG. 6 shows this monitor looking at the side of a person's head. The middle third of FIG. 6 shows this monitor looking at the front of a person's head. The bottom third of FIG. 6 shows this monitor looking down at the top of a person's head.

As shown in the top third of FIG. 6, this brain activity monitor comprises: an arcuate frame which is configured to be worn on a person's head, wherein this arcuate frame further comprises: a left ear loop 6005 which is configured to curve around the person's left ear; a posterior loop 6007 which is connected to the left ear loop 6005, where this posterior loop 6007 is configured to curve around a posterior portion of a person's head; a left upward-extending member 6003 which is configured to loop upward toward the top of the person's head from the left ear loop 6005 and then back downward to left ear loop 6005, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 6001, 6002, 6021, and 6022, which collect data concerning electromagnetic brain activity; and a left-side housing 6006 which contains a power source, a data processing unit, and a data transmitter and/or receiver.

The middle third and bottom third of FIG. 6 show this same hair-engaging mobile brain activity monitor from a frontal face perspective and a top-down perspective, respectively. Right-side components include: a right ear loop 6015 which is configured to curve around the person's right ear; a right upward-extending member 6013 which is configured to loop upward toward the top of the person's head from the right ear loop 6015 and then back downward to right ear loop 6015, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 6011, 6012, 6031, and 6032, which collect data concerning electromagnetic brain activity. In this example, the upper tips of right and left upward-extending members are not connected or attached to each other, even in the second configuration. Relevant example and design variations discussed elsewhere in this disclosure can also be applied to the example shown here in FIG. 6.

Figure 7:
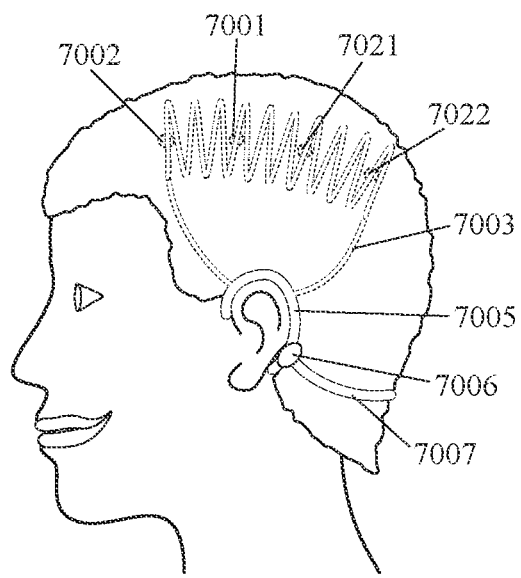
FIG. 7 shows a BCI device with right and left side members with teeth which engage a person's hair.
Figure 7:
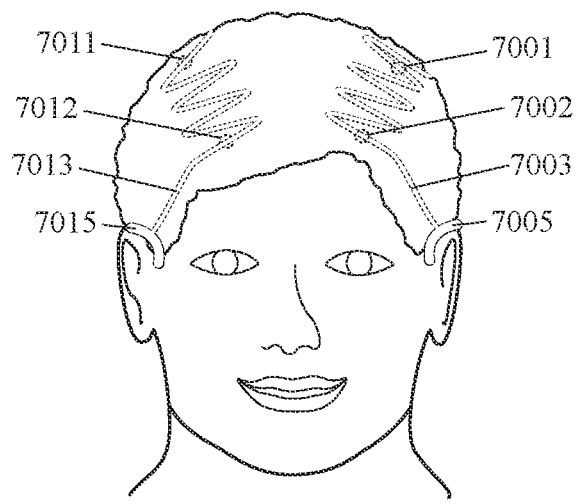
Figure 7:
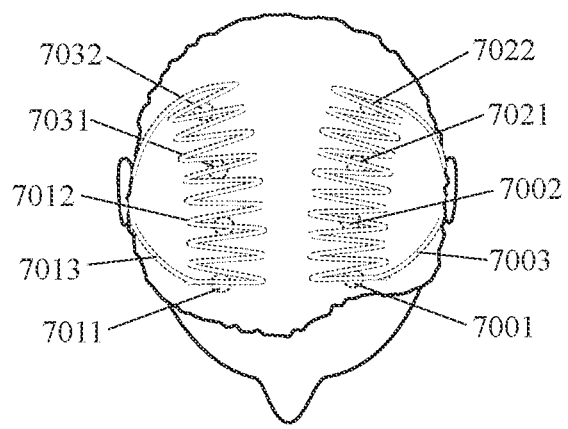

FIG. 7 shows another example of how this invention can be embodied in a hair-engaging mobile brain activity monitor. The monitor shown in this example is similar to the one shown in FIG. 6 except that the upward-extending member is a loop with multiple upward-facing protrusions, prongs, and/or teeth. The top third of FIG. 7 shows this monitor looking at the side of a person's head. The middle third of FIG. 7 shows this monitor looking at the front of a person's head. The bottom third of FIG. 7 shows this monitor looking down at the top of a person's head.

As shown in the top third of FIG. 7, this brain activity monitor comprises: an arcuate frame which is configured to be worn on a person's head, wherein this arcuate frame further comprises: a left ear loop 7005 which is configured to curve around the person's left ear; a posterior loop 7007 which is connected to the left ear loop 7005, where this posterior loop 7007 is configured to curve around a posterior portion of a person's head; a left upward-extending member 7003 which is configured to loop upward toward the top of the person's head from the left ear loop 7005 and then back downward to left ear loop 7005, wherein this left upward-extending member has multiple upward-facing protrusions, prongs, and/or teeth, wherein this left upward-extending member has a first configuration in which its upper-most portion is a first distance from the top of the person's head, wherein this left upward-extending member has a second configuration in which its upper-most portion is a second distance from the top of the person's head, wherein the second distance is less than the first distance, and wherein the left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 7001, 7002, 7021, and 7022, which collect data concerning electromagnetic brain activity; and a left-side housing 7006 which contains a power source, a data processing unit, and a data transmitter and/or receiver.

The middle third and bottom third of FIG. 7 show this same hair-engaging mobile brain activity monitor from a frontal face perspective and a top-down perspective, respectively. Right-side components include: a right ear loop 7015 which is configured to curve around the person's right ear; a right upward-extending member 7013 which is configured to loop upward toward the top of the person's head from the right ear loop 7015 and then back downward to right ear loop 7015, wherein this right upward-extending member has multiple upward-facing protrusions, prongs, and/or teeth, wherein this right upward-extending member has a first configuration in which its upper-most portion is a first distance from the top of the person's head, wherein this right upward-extending member has a second configuration in which its upper-most portion is a second distance from the top of the person's head, wherein the second distance is less than the first distance, and wherein the right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 7011, 7012, 7031, and 7032, which collect data concerning electromagnetic brain activity. In this example, the upper tips of right and left upward-extending members are not connected or attached to each other, even in the second configuration. Relevant example and design variations discussed elsewhere in this disclosure can also be applied to the example shown here in FIG. 7.

Figure 8:
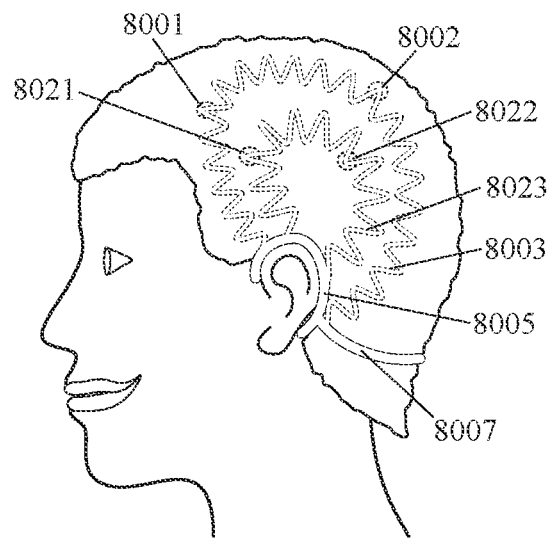
FIG. 8 shows a BCI device with right and left side nested loops which engage a person's hair.
Figure 8:
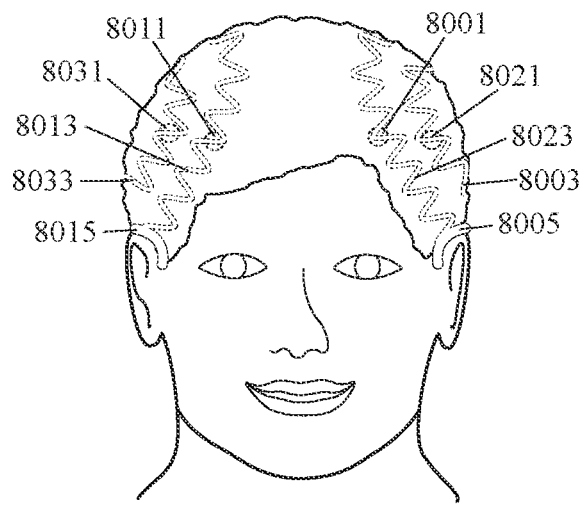
Figure 8:
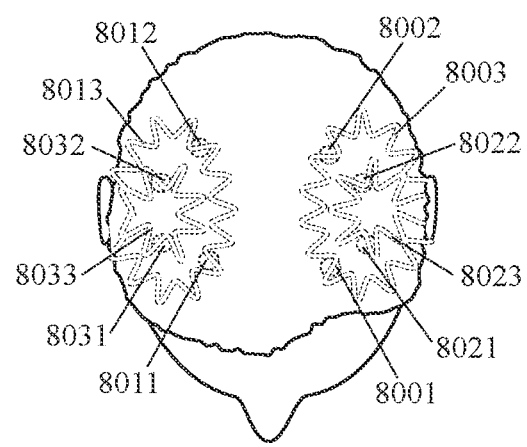

FIG. 8 shows another example of how this invention can be embodied in a hair-engaging mobile brain activity monitor. The monitor shown in this example is similar to the one shown in FIG. 7 except that there are two nested upward-extending loops with multiple protrusions, prongs, and/or teeth. The top third of FIG. 8 shows this monitor looking at the side of a person's head. The middle third of FIG. 8 shows this monitor looking at the front of a person's head. The bottom third of FIG. 8 shows this monitor looking down at the top of a person's head.

As shown in the top third of FIG. 8, this brain activity monitor comprises: an arcuate frame which is configured to be worn on a person's head, wherein this arcuate frame further comprises: a left ear loop 8005 which is configured to curve around the person's left ear; a posterior loop 8007 which is connected to the left ear loop 8005, where this posterior loop 8007 is configured to curve around a posterior portion of a person's head; a first left upward-extending member 8003 which is configured to loop upward toward the top of the person's head from the left ear loop 8005 and then back downward to left ear loop 8005, wherein this first left upward-extending member has multiple protrusions, prongs, and/or teeth, wherein this first left upward-extending member has a first configuration in which its upper-most portion is a first distance from the top of the person's head, wherein this first left upward-extending member has a second configuration in which its upper-most portion is a second distance from the top of the person's head, wherein the second distance is less than the first distance, and wherein the first left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; a second left upward-extending member 8023 which is configured to loop upward toward the top of the person's head from the left ear loop 8005 and then back downward to left ear loop 8005, wherein this second left upward-extending member has multiple protrusions, prongs, and/or teeth, wherein this second left upward-extending member has a first configuration in which its upper-most portion is a first distance from the top of the person's head, wherein this second left upward-extending member has a second configuration in which its upper-most portion is a second distance from the top of the person's head, wherein the second distance is less than the first distance, and wherein the second left upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; one or more left-side electromagnetic energy sensors, 8001, 8002, 8021, and 8022, which collect data concerning electromagnetic brain activity; and a left-side housing 8006 which contains a power source, a data processing unit, and a data transmitter and/or receiver.

The middle third and bottom third of FIG. 8 show this same hair-engaging mobile brain activity monitor from a frontal face perspective and a top-down perspective, respectively. Right-side components include: a right ear loop 8015 which is configured to curve around the person's right ear; a first right upward-extending member 8013 which is configured to loop upward toward the top of the person's head from the right ear loop 8015 and then back downward to right ear loop 8015, wherein this first right upward-extending member has multiple protrusions, prongs, and/or teeth, wherein this first right upward-extending member has a first configuration in which its upper-most portion is a first distance from the top of the person's head, wherein this first right upward-extending member has a second configuration in which its upper-most portion is a second distance from the top of the person's head, wherein the second distance is less than the first distance, and wherein the first right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; a second right upward-extending member 8033 which is configured to loop upward toward the top of the person's head from the right ear loop 8015 and then back downward to right ear loop 8015, wherein this second right upward-extending member has multiple protrusions, prongs, and/or teeth, wherein this second right upward-extending member has a first configuration in which its upper-most portion is a first distance from the top of the person's head, wherein this second right upward-extending member has a second configuration in which its upper-most portion is a second distance from the top of the person's head, wherein the second distance is less than the first distance, and wherein the second right upward-extending member is configured to engage hair (e.g. extend under a layer of hair, interlock with hair, latch onto hair, mesh with hair, slide between hair layers, slide between hair strands, slide into or under hair, and/or slide under a layer of hair) in the second configuration; and one or more right-side electromagnetic energy sensors, 8011, 8012, 8031, and 8032, which collect data concerning electromagnetic brain activity. In this example, the upper tips of right and left upward-extending members are not connected or attached to each other, even in the second configuration. Relevant example and design variations discussed elsewhere in this disclosure can also be applied to the example shown here in FIG. 8.

In an example, this invention can be embodied in a Brain Computer Interface (BCI) method which enables a person to control environmental devices, appliances, and/or machines in different action modes based on common electromagnetic brain activity patterns which are associated with the same control command across different action modes. In different embodiments, one or more action modes can be selected from the group consisting of: speaking a word, phrase, and/or command; using a touch screen or other touch-based human-to-computer interface; manually moving a switch, button, dial, or knob on an environmental device; making a hand gesture; typing a word, phrase, and/or command; moving a computer mouse; moving one's eyes; and just thinking about controlling an environmental device.

In an example, a Brain Computer Interface (BCI) method can comprise: two or more calibration periods in which a person controls an environmental device in a selected manner by performing actions in two or more different action modes; and a subsequent period in which the person controls the environmental device in the selected manner by performing an action in an action mode which is more convenient, efficient, and/or discreet than either of the first two action modes. In an example, the action mode in the subsequent period can be just thinking about controlling the environmental device in the selected manner. In an example, this invention can be part of the Internet of Thinks (IoT).

In an example, this invention can be embodied in a Brain Computer Interface (BCI) system comprising: a head-worn attachment; at least one electromagnetic brain activity sensor; a microphone; a touch screen; and a data processing unit. In this example, the data processing unit: (a) analyzes electromagnetic brain activity from a first time period within which the person speaks a word or phrase to control an environmental device, appliance, and/or machine in a selected manner; (b) analyzes electromagnetic brain activity from a second period within which the person uses the touch screen to control the environmental device, appliance, and/or machine in the selected manner; (c) identifies a specific pattern shared by electromagnetic brain activity within the first and second periods of time which is associated with controlling the environmental device, appliance, and/or machine in the selected manner; and (d) if the data processing unit detects that specific pattern of electromagnetic brain activity within a third time period, then the data processing unit controls the environmental device, appliance, and/or machine in the selected manner.

In an example, during the third time period the person neither speaks a word or phrase nor uses a touch screen in order to control the environmental device, appliance, and/or machine in the selected manner. In an example, during the third time period, the person can control the device, appliance, and/or machine in the selected manner via an external action selected from the group consisting of: using their hand to move a switch, button, dial, or knob on the device; making a hand gesture; typing a word or phrase; moving a computer mouse; and moving their eyes. In an example, during the third time period, the person can control the device, appliance, and/or machine in the selected manner by just thinking, unaccompanied by any of these external actions.

In this example, this invention includes a microphone and has speech recognition capability in order to recognize selected words, phrases, and/or commands which are spoken by the person wearing the device. In an example, this invention can further comprise a database of selected words, phrases, and/or commands which are spoken by the person wearing the device. In an example, commands can relate to controlling environmental devices, appliances, and/or machines. In an example, a database can comprise sets of different words or phrases which share the same command meaning (such as sets of phrases with the same words in different orders or sets of phrases with word synonyms).

In an example, a database can associate specific electromagnetic brain activity patterns with specific words, phrases, and/or commands. In an example, a data processing unit can analyze data from the electromagnetic brain activity sensor and analyze data from the microphone in order to associated specific patterns of electromagnetic brain activity with specific words, phrases, and/or commands. In this example, there is a calibration period in which a data processing unit identifies a person's specific electromagnetic brain activity pattern which is associated with the person speaking a specific word, phrase, and/or command.

In an example, a database can associate a specific electromagnetic brain activity pattern with a noun which represents a selected environmental device, appliance, and/or machine. For example, there can be specific electromagnetic brain activity patterns associated, respectively, with nouns such as "Light", or "Temperature", "Dishwasher", "Edgar," or "Door". In an example, a database can associate a specific electromagnetic brain activity pattern with a verb, adjective, or preposition which represents a change in an environmental device, appliance, and/or machine. For example, there can be specific electromagnetic brain activity patterns associated, respectively, with the words such as "On", "Off", "Up", "Down", "Open", "Close", "Buy", and "Sell". In an example, a database can associate a specific electromagnetic brain activity pattern with a command which is a combination of a noun plus a verb, adjective, or preposition. For example, there can be specific electromagnetic brain activity patterns associated, respectively, with commands such as "Light On", "Light Off", "Light Up", "Light Down", "Temperature Up," "Temperature Down", "Droids Not", "Dishwasher On", "Edgar On", "Door Open", and "Door Close". In an example, word order can be reversed in a command.

In an example, specific electromagnetic brain activity patterns can be identified based on data from electromagnetic brain activity sensors which are positioned by a head-worn attachment on the surface portion of a person's head which is closest to Broca's area in the brain. In an example, electromagnetic brain activity sensors can be positioned at one or more locations selected from the group of standard EEG electrode placement sites consisting of: C3, C4, Cz, F7, T3, and T4. In an example, these sensors can be positioned by a head-worn attachment on the surface portion of a person's head which is closest to Wernicke's area in the brain. In an example, the locations of multiple electromagnetic brain activity sensors on a person's head can be automatically adjusted for a particular person to optimize recognition of that person's brain activity patterns. In an example, the locations of multiple electromagnetic brain activity sensors on a person's head can be automatically adjusted by actuators based on which application is operating at a given time.

In this embodiment, this invention also includes a touch-based human-to-machine interface which the person uses to control an environmental device, appliance, and/or machine. In an example, this interface can be a touch screen (e.g. a touch-responsive display screen). In an example, a touch screen can be part of a mobile hand-held computing device or part of a wearable computing device. In an example, this touch screen can be responsive to touch by the person's fingers. In a variation on this embodiment, this invention can comprise a touch-based human-to-machine interface which is not a display screen. In an example, this interface can be touch-responsive fabric and/or a touch-responsive surface which is integrated into an article of clothing. In an example, this interface can be a wearable computing device which does not have a touch screen, but does have a touch-responsive surface.

In an example, the data processing unit can know when a person moves their finger on a touch screen in order to control the operation of an environmental device, appliance, and/or machine. In an example, a data processing unit can know when a person uses a touch screen on a hand-held device because the data processing unit is in wireless communication with the hand-held device. For example, this invention can recognize when a person uses a touch screen to turn lights on or off In an example, this invention can know when a person uses a finger to open an application on a hand-held or wearable device in order to adjust environmental lighting, temperature, door access, music, communication mode, and so forth. In an example, this invention can be in wireless communication with a separate hand-held or wearable mobile device in order to know when such touch-based environmental control actions occur.

In an example, this invention can create a database of specific touch-screen actions performed by a person for controlling environmental devices, appliances, and/or machines. In an example, these touch-screen actions can be within one or more environmental control applications on a mobile device. In an example, these touch-screen actions can be within one or more commerce and/or financial control applications on a mobile device. In an example, a database can associate specific electromagnetic brain activity patterns with specific touch-screen actions, respectively.

In an example, there can be a learning and/or calibration period in which a data processing unit identifies a person's specific electromagnetic brain activity pattern which is associated with the person performing a specific touch screen control action with respect to an environmental device. In an example, a database can include touch-screen actions such as: opening a home environmental control application and adjusting home temperature; opening a home lighting control application and turning lights on or off and opening a commerce application and purchasing an item. In an example, this database can further include words, phrases, and/or commands which represent these touch screen control actions, such as "Temperature Up", "Lights On", "Open Door", and "Buy It".

In an example, a head-worn attachment can be worn on (or within) a person's ear, incorporated into eyewear, or worn like a headband. In an example, a head-worn attachment can be worn on, around, or in a person's ear. In an example, a head-worn attachment can be selected from the group consisting of: ear bud, ear clip, ear plug, hearing aid, ear ring, ear phone, ear muff, headphones, headband, and headset. In an example, a head-worn attachment can be inserted (at least partially) into an ear canal. In an example, a head-worn attachment can be attached or clipped to an ear lobe. In an example, this invention can comprise only one head-worn attachment which is on one side of a person's head. In an example, a head-worn attachment can span both sides of a person's head. In an example, this invention can comprise two head-worn attachments, one on each side of a person's head.

In an example, a head-worn attachment can span the upper, rear, or front surface of the portion of a person's ear which connects the auricle to the main body of the person's head. In an example, a head-worn attachment can span the upper and rear surfaces of the portion of a person's ear which connects the auricle to the main body of the person's head. In an example, a head-worn attachment can span the upper and front surfaces of the portion of a person's ear which connects the auricle to the main body of the person's head.

In an example, a head-worn attachment can span between 5% and 25% of the cross-sectional perimeter of the portion of the person's ear which connects the auricle to the main body of the person's head. In an example, a head-worn attachment can span between 5% and 25% of the circumference of the portion of the person's ear which connects the auricle to the main body of the person's head. In an example, a head-worn attachment can span between 25% and 50% of the cross-sectional perimeter of the portion of the person's ear which connects the auricle to the main body of the person's head. In an example, a head-worn attachment can span between 25% and 50% of the circumference of the portion of the person's ear which connects the auricle to the main body of the person's head.

In an example, a head-worn attachment can span between 50% and 75% of the cross-sectional perimeter of the portion of the person's ear which connects the auricle to the main body of the person's head. In an example, a head-worn attachment can span between 50% and 75% of the circumference of the portion of the person's ear which connects the auricle to the main body of the person's head. In an example, a head-worn attachment can span between 75% and 100% of the cross-sectional perimeter of the portion of the person's ear which connects the auricle to the main body of the person's head. In an example, a head-worn attachment can span between 75% and 100% of the circumference of the portion of the person's ear which connects the auricle to the main body of the person's head.

In an example, clockwise polar coordinates can be defined for an ear, with 0 degrees being the upper-most location where the auricle connects to the main body of the head and 180 degrees being the lower-most location where the auricle connects to the main body of the head. In an example, a head-worn attachment can curve around an ear from a first polar location to a second polar location. In an example, the first polar location can be within the range of 270-350 degrees and the second polar location can be within the range of 10-90 degrees. In an example, the first polar location can be within the range of 270-350 degrees and the second polar location can be within the range of 90-200 degrees In an example, a head-worn attachment can be eyewear. In an example, a head-worn attachment can be selected from the group consisting of: eyeglasses, goggles, visor, monocle, contact lens, VR glasses, AR glasses, and other eyewear. In an example, a head-worn attachment can span from one ear to the other ear across a person's forehead. In an example, a head-worn attachment can span both eyes. In an example, a head-worn attachment can span eyebrows. In an example, a head-worn attachment can span from one ear to the other ear across a person's face. In an example, an eyewear head-worn attachment can be one continuous piece. In an example, an eyewear head-worn attachment can be comprised of multiple connected pieces. In an example, an eyewear head-worn attachment can be comprised of multiple hinge-connected pieces. In an example, an eyewear head-worn attachment can be comprised of multiple flexibly-connected pieces.

In an example, a head-worn attachment can be a headband. In an example, a head-worn attachment can encircle a person's head in a horizontal manner plane when the person's head is upright. In an example, a head-worn attachment can encircle a person's head at an acute angle with respect to this horizontal plane, wherein this acute angle is within a range of 1-10 degrees. In an example, this angle can be within a range of 10-20 degrees. In an example, this angle can be within a range of 20-45 degrees. In an example, a head-worn attachment can span at least 30% of the circumference of the head at an acute angle with respect to a horizontal plane when the person's head is upright, wherein this acute angle is within the range of 1-10 degrees. In an example, this angle can be in the range of 10-20 degrees. In an example, this angle can be within a range of 20-45 degrees.

In an example, a head-worn attachment can be selected from the group consisting of: headband, hair band, hair clip, hair comb, hat, cap, tiara, frontal loop, and rear loop. In an example, a head-worn attachment can be worn at least partially under a person's hair. In an example, a head-worn attachment can have teeth or other protrusions which engage a person's hair. In an example, a head-worn attachment can be circular, elliptical, or oval. In an example, a head-worn attachment can be shaped like a semi-circle or three-quarters of a circle. In an example, a head-worn attachment can be arcuate. In an example, a head-worn attachment can be sinusoidal. In an example, a head-worn attachment can span from one ear to the other ear, over the top of the head. In an example, a head-worn attachment can span from one ear to the other ear, around the rear of the head. In an example, a head-worn attachment can have a first portion which spans from one ear to the other ear over the top of the head and a second portion which spans from one ear to the other ear around the rear of the head. In an example, a head-worn attachment can have a first portion which spans from one ear to the other ear over the top of the head and a second portion which spans from one ear to the other ear around the front of the head.

In an example, at least one electromagnetic brain activity sensor can be held in proximity to a person's head by the head-worn attachment. In an example, electromagnetic brain activity sensors can be a part of the head-worn attachment. In an example, one or more electromagnetic brain activity sensors can be modular and removably attached to the head-worn attachment. In an example, the locations of one or more electromagnetic brain activity sensors with respect to a head-worn attachment can be manually or automatically adjusted. In an example, the proximity of an electromagnetic brain activity sensor to a person's head can be manually or automatically adjusted. In an example, each electromagnetic brain activity sensor can be paired with a nearby signal amplifier. In an example, an amplifier can amplify voltage signals between the first and second (reference) electrodes by 2-5 orders of magnitude.

In an example, an electromagnetic brain activity sensor can measure electromagnetic energy emitted by a person's brain. In an example, an electromagnetic brain activity sensor can measure changes in electromagnetic energy flowing between two electrodes wherein these changes are due to electromagnetic brain activity. In an example, an electromagnetic brain activity sensor can measure voltage fluctuations resulting from ionic current within the neurons of the brain. In an example, an electromagnetic brain activity sensor can be an electroencephalography (EEG) sensor.

In an example, an electromagnetic brain activity sensor can be a capacitive sensor. In an example, an electromagnetic brain activity sensor can be a dry electrode. In an example, an electromagnetic brain activity sensor can be a wet electrode. In an example, an electromagnetic brain activity sensor can measure voltage fluctuations between a first electrode and a second (reference) electrode due to electromagnetic brain activity. In an example, voltage differences between a first electrode and a second (reference) electrode can be called a "channel" In an example, a set of channels can be called a "montage." In an example, a second (reference) electrode can be attached to an ear. In an example, there can be two reference electrodes in a system, one attached to each ear.

In an example, an electromagnetic brain activity sensor can be positioned by a head-worn attachment on the surface portion of the person's head which is closest to Broca's area of the brain. In an example, one or more electromagnetic brain activity sensors can be positioned by the head-worn attachment at one or more locations selected from the group of standard EEG electrode placement sites consisting of: C3, C4, Cz, F7, T3, and T4. In an example, an electromagnetic brain activity sensor can be positioned by a head-worn attachment on the surface portion of the person's head which is closest to Wernicke's area of the brain. In an example, an electromagnetic brain activity sensor can be positioned by a head-worn attachment on the surface portion of the person's head which is closest to the homunculus and/or primary motor cortex of the brain. In an example, multiple electromagnetic brain activity sensors can be positioned by a head-worn attachment on the surface portions of the person's head which are closest to the superior temporal gyrus and the supramarginal gyrus.

In an example, one or more electromagnetic brain activity sensors or channels can be located on a person's head so as to most accurately measure the activity of one or more brain areas selected from the group consisting of: Broca's area (of the Frontal Lobe), Wernicke's area (of the Occipital Lobe), Cerebellum, Cerebral Cortex, Frontal Lobe, Occipital Lobe, Parietal Lobe, and Temporal Lobe. In an example, one or more electromagnetic brain activity sensors or channels can be placed at one or more electrode placement sites selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2. In an example, an electromagnetic brain activity sensor can be placed within an ear canal or attached to the auricle. In an example, an electromagnetic brain activity sensor can be positioned by the head-worn attachment on a person's temple and/or forehead.

In this example, this invention also includes a data processing unit. In an example, a data processing unit can be a microchip, microprocessor, circuit board, CPU, computer, or other computing device. In an example, a data processing unit can be a part of (or directly attached to) a head-worn attachment. In an example, a data processing unit can be in direct electromagnetic communication with an electromagnetic brain activity sensor.

In an example, this invention can comprise a wireless data transmitter and/or receiver. In an example, a data processing unit can be separate from a head-worn attachment. In an example, a data processing unit can be in a remote location. In an example, a data processing unit can be in wireless communication with an electromagnetic brain activity sensor. In an example, a data processing unit can be part of a remote computing device selected from the group consisting of: electronically-functional wrist band (e.g. a "smart watch"), electronically-functional eyewear (e.g. "smart glasses"), electronically-functional clothing (e.g. "smart clothing"), electronically-functional shoes (e.g. "wise sole"), other wearable device, wearable data processing hub, mobile computer, electronic tablet, electronic pad, mobile phone, smart phone, internet-connected remote computer, communication network tower, satellite, home control system, and implanted medical device.

In an example, this invention can comprise two data processing units: a first data processing unit which is part of the head-worn attachment (in direct electromagnetic communication with an electromagnetic brain activity sensor) and a second data processing unit which is not part of the head-worn attachment (but is in wireless communication with the first unit). In an example, a first set of data processing functions can be performed by the first data processing unit and a second set of data processing functions can be performed by the second data processing unit. In an example, a first data processing unit can be in wireless electromagnetic communication with a second data processing unit in a mobile hand-held device and the operation of this invention can be controlled by an application on the mobile device. In an example, a first data processing unit can be in wireless electromagnetic communication with a second data processing unit in a wearable electronic hub device and the operation of this invention can be controlled by an application on the hub device.

In an example, this invention can further comprise a power source and/or power transducer which supplies power to the electromagnetic brain activity sensor and/or the data processing unit. In an example, a power source can be a battery. In an example, a power source and/or power transducer can transduce, harvest, and/or generate energy from body motion or kinetic energy. In an example, a power source and/or power transducer can transduce, harvest, and/or generate energy from ambient light energy. In an example, a power source and/or power transducer can transduce, harvest, and/or generate energy from body thermal energy. In an example, a power source and/or power transducer can transduce, harvest, and/or generate energy from ambient electromagnetic energy.

In an example, this invention can have components which enable it to detect actions in other modes for controlling environmental devices, appliances, and/or machines. In an example, this invention can include a body motion sensor or communication interface to detect a manual action to control an environmental device, appliance, and/or machine. In an example, this invention can recognize body motions which comprise manual control of an environmental device. For example, this invention can recognize when a person uses their hand to move a wall switch to turn lights on, to insert a key to unlock a door, or to turn a door knob to open a door. In an example, this invention can recognize when a person uses their hand to move a switch, knob, dial, button, or other control structure on an environmental device in order to turn that device on or off, adjust the device's power level, or otherwise adjust device operation. In an example, this invention can be in wireless communication with an environmental device in order to receive communication from that device when a person moves a switch, knob, dial, button, or other control structure on that device. For example, if the person turns a knob on a dishwasher in order to turn the dishwasher on, then this can be wirelessly communicated to this invention so that this invention knows that this manual control action has occurred.

In an example, this invention can create a database of manual actions to control environmental devices which are performed by the person wearing the device. In an example, this database can also include specific electromagnetic brain activity patterns which are associated with those manual control actions. In an example, this database can also include specific words, phrases, and/or commands which are associated with those manual control actions. In an example, a data processing unit can analyze data from an electromagnetic brain activity sensor and analyze data from a body motion sensor and/or wireless communication from an environmental device in order to associate specific patterns of electromagnetic brain activity with specific manual control actions for environmental devices. In an example, there can be a calibration period in which a data processing unit identifies a person's specific electromagnetic brain activity pattern which is associated with the person performing a specific manual control action with respect to an environmental device.

In an example, a database can include manual control actions such as: turning on a light with a wall switch; turning on a dishwasher by rotating a knob on the dishwasher; unlocking a door by inserting a key; opening a door by turning a door knob; and changing a temperature setting on a thermostat by rotating a dial. In an example, there can also be words, phrases, or commands which are associated with these manual actions in the database—such as "Light On", "Dishwasher On", "Door Open", and "Temperature Up".

In an example, this invention can have components which enable it to detect actions in other modes for controlling environmental devices, appliances, and/or machines. In an example, this invention can include a mechanism for recognizing hand gestures. In an example, this invention can recognize hand gestures via one or more motion sensors, infrared light sensors, ultrasound sensors, radar sensors, EMG sensors, or cameras. In an example, this invention can create a database of hand gestures to control environmental devices which are performed by the person wearing the device. In an example, a specific hand gesture can represent a specific environmental device, appliance, and/or machine. In an example, a specific hand gesture can represent a specific change in the operation of environmental device, appliance, and/or machine. In an example, this database can also include specific electromagnetic brain activity patterns which are associated with those hand gestures. In an example, this database can also include specific words, phrases, and/or commands which are associated with those hand gestures. In an example, a data processing unit can analyze data from an electromagnetic brain activity sensor and analyze data from a hand gesture detector in order to associate specific patterns of electromagnetic brain activity with specific hand gesture control actions for environmental devices.

In an example, a hand gesture detector can recognize one or more hand gestures selected from the group consisting of: "finger tap" (palm facing down with index tip moving down and up once); "finger double tap" (palm facing down with index tip moving down and up twice quickly); "finger press" (palm facing down with index tip pressing down for extended time); "finger slide right" (palm facing down with index or middle tip moving right and arcing left); "finger slide left" (palm facing down with index or middle tip moving left and arcing right); "finger rub" (palm facing down with index or middle tip moving back and forth); "finger scroll down" (palm facing down with index or middle tip moving down and arcing up); "finger scroll up" (palm facing down with index or middle tip moving up and arcing down); "finger clockwise" (index or middle tip moving in a clockwise circle or arc of a circle); "finger counterclockwise" (index or middle tip moving in a counterclockwise circle or arc of a circle); "finger figure eight" (index or middle tip moving in a figure eight); "finger pinch" (thumb and index or middle tip moving closer); "finger spread" (thumb and index or middle tip moving apart); "finger merge" (index tips from both hands moving together); "finger divide" (index tips from both hands moving apart); "grasp" (thumb and aligned fingers touch to form a "C"); "drink" (thumb and aligned fingers form a "C" and hand rotating toward person); "grab" (thumb and four fingers contracting simultaneously); "move down" (palm facing down with hand pivoting downward from wrist and/or elbow); "move up" (palm facing up with hand pivoting upward from wrist and/or elbow); "move right" (palm facing sideways with hand pivoting rightward from wrist); "move left" (palm facing sideways with hand pivoting leftward from wrist); "hand rotation clockwise" (flat hand rotating clockwise); "hand rotation counter-clockwise" (flat hand rotating counter-clockwise); "hold and turn clockwise" (fist with thumb and index extended and rotating clockwise); "hold and turn counter-clockwise" (fist with thumb and index extended and rotating counter-clockwise); "outward palm" (flat hand with palm outward and thumb and all fingers extended); "hand wave" (flat hand with palm outward and side-to-side motion); "chop" (flat hand with palm downward and side-to-side motion); "fist" (thumb and all fingers contracted); "fist pump" (upright fist moving up and down); "fist bang or fist bump" (extended fist moving down and up); "knock" (fist pivoting downward from wrist); "thumbs down" (fist with thumb extended downwards); "thumbs up" (fist with thumb extended upward); "point" (fist with index tip extended outward); "gun" (vertical fist with index and middle extended outward together); "V" or "peace sign" (outward-facing fist with index and middle extended upwards apart); "scissors" (fist with index and middle apart and then together); "Vulcan salute" (outward-facing palm with fingers up and separated between middle and ring); "cuckold/horns" (hand vertical with index and pinky upward); "me ape" (upward fist with middle extended upward); "call me" (vertical fist with thumb and pinky extended); "hang loose" (horizontal palm with thumb and pinky extended); "I Love You" (thumb, index, and pinky extended while middle and ring touch palm); "OK" (thumb and index form a circle); "loser" (fist with thumb and index finger extended at a right angle); "no" (fist with raised extended index moving side to side); "finger cross" (thumb and middle fingers crossed); "finger snap" (middle sliding quickly from tip to base of thumb); "money" (tips of middle and thumb rubbing back and forth on each other); "come here" (upward or sideways facing fist with index tip extended and moving inward); "blah blah" (thumb and horizontal extended fingers opening and closing together); "world's smallest violin" (fist with thumb and index extended and rubbing); "writing" (fist with thumb and index touching and moving together); "thumb to index" (thumb tip touching index finger tip); "thumb to middle" (thumb tip touching middle finger tip); "thumb to ring" (thumb tip touching ring finger tip); "thumb to pinky" (thumb tip touching pinky tip); a gesture indicating a selected letter in sign language; and a gesture indicating a selected word in sign language.

In an example, this invention can have components which enable it to detect actions in other modes for controlling environmental devices, appliances, and/or machines. In an example, this invention can include a physical keyboard, physical keypad, light-projected keypad, virtual keypad, or other typing interface which enables a person to type commands to control environmental devices, appliances, and/or machines. In an example, a keyboard or keypad can be part of a hand-held device with which a head-worn device is in wireless communication. In an example, a keyboard or keypad can be part of a separate wearable device (such as a smart watch or wearable technology hub) with which a head-worn device is in wireless communication. In an example, this invention can create a database of words, phrases, or commands to control environmental devices which are typed by the person wearing the device. In an example, this database can also include specific electromagnetic brain activity patterns which are associated with those words, phrases, or commands. In an example, this invention can include a computer mouse which enables a person to control environmental devices, appliances, and/or machines. In another example, this invention can include an eye gaze tracker which enables a person to control environmental devices, appliances, and/or machines by moving their eyes.

The data processing unit of this invention analyzes electromagnetic brain activity signals during different periods of time in order to identify common patterns which occur during actions for the same control purpose across different action modes. In an example, a pattern of electromagnetic brain activity which is associated with an action to control an environmental device can be a transient and/or non-recurring pattern of electromagnetic brain activity. In an example, a transient pattern of electromagnetic brain activity can be a sequence of spikes or waves which do not repeat. In an example, parameters used to identify a non-repeating pattern of electromagnetic brain activity can be selected from the group consisting of: shape of one or more spikes; amplitude, maximum, or minimum of one or more spikes; frequency of multiple spikes; pattern covariation; pattern entropy; pattern signature; first and second order differentials; polynomial modeling; and composite sine wave modeling.

In an example, a transient pattern of electromagnetic brain activity which is associated with an action to control an environmental device can be identified using one or more analytical methods which are selected from the group consisting of: Analysis of Variance (ANOVA), Artificial Neural Network (ANN), Auto-Regressive (AR) Modeling, Bayesian Analysis, Bonferroni Analysis (BA), Centroid Analysis, Chi-Squared Analysis, Cluster Analysis, Correlation, Covariance, Data Normalization (DN), Decision Tree Analysis (DTA), Discrete Fourier transform (DFT), Discriminant Analysis (DA), Empirical Mode Decomposition (EMD), Factor Analysis (FA), Fast Fourier Transform (FFT), Feature Vector Analysis (FVA), Fisher Linear Discriminant, Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inter-Band Power Ratio, Inter-Channel Power Ratio, Inter-Montage Power Mean, Inter-Montage Ratio, Kalman Filter (KF), Kernel Estimation, Laplacian Filter, Laplacian Montage Analysis, Least Squares Estimation, Linear Regression, Linear Transform, Logit Model, Machine Learning (ML), Markov Model, Maximum Entropy Modeling, Maximum Likelihood, Mean Power, Multi-Band Covariance Analysis, Multi-Channel Covariance Analysis, Multivariate Linear Regression, Multivariate Logit, Multivariate Regression, Naive Bayes Classifier, Neural Network, Non-Linear Programming, Non-negative Matrix Factorization (NMF), Power Spectral Density, Power Spectrum Analysis, Principal Components Analysis (PCA), Probit Model, Quadratic Minimum Distance Classifier, Random Forest (RF), Random Forest Analysis (RFA), Regression Model, Signal Amplitude (SA), Signal Averaging, Signal Decomposition, Sine Wave Compositing, Singular Value Decomposition (SVD), Spine Function, Support Vector Machine (SVM), Time Domain Analysis, Time Frequency Analysis, Time Series Model, Trained Bayes Classifier, Variance, Waveform Identification, Wavelet Analysis, and Wavelet Transformation.

In an example, a transient pattern of electromagnetic brain activity can start to occur with a specified period of time before an action. In an example, this period of time can be under one minute. In an example, this period of time can be in the range of 1-10 seconds. In an example, this period of time can be different for different action modes. In an example, a transient pattern of electromagnetic brain activity which is associated with an action to control an environmental device can be a transient and/or non-recurring pattern of electromagnetic activity which is concurrent with the action.

In an example, a pattern of electromagnetic brain activity which is associated with an action to control an environmental device can be the start of a repeating electromagnetic brain activity pattern or waveform. In an example, a pattern of electromagnetic brain activity which is associated with an action to control an environmental device can be a change in an already-occurring repeating electromagnetic brain activity pattern or waveform (e.g. "brainwaves"). In an example, a repeating electromagnetic brain activity pattern can be an oscillatory pattern. In an example, a repeating electromagnetic brain activity pattern can be modeled as a composite of multiple sine waves. In an example, a repeating electromagnetic brain activity pattern can be decomposed into subpatterns in different frequency bands. In an example, these frequency bands can be selected from the group consisting of: Delta, Theta, Alpha, Beta, and Gamma.

Ongoing brain waveforms classified as Delta waves can be within a frequency band selected from the group consisting of: 0.5-3.5 Hz, 0.5-4 Hz, 1-3 Hz, 1-4 Hz, and 2-4 Hz. Ongoing brain waveforms classified as Theta waves can be within a frequency band selected from the group consisting of: from the group consisting of: 3.5-7 Hz, 3-7 Hz, 4-7 Hz, 4-7.5 Hz, 4-8 Hz, and 5-7 Hz. Ongoing brain waveforms classified as Alpha waves can be within a frequency band selected from the group consisting of: 7-13 Hz, 7-14 Hz, 8-12 Hz, 8-13 Hz, 7-11 Hz, 8-10 Hz, and 8-10 Hz. Ongoing brain waveforms classified as Beta waves can be within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. Ongoing brain waveforms classified as Gamma waves can be within a frequency band selected from the group consisting of: group consisting of: 30-100 Hz, 35-100 Hz, 40-100 Hz, and greater than 30 Hz.

In an example, the selection of which frequency band or bands are most useful for identifying a pattern of electromagnetic brain activity associated with a control action can be identified during a calibration period. In an example, complex repeating patterns can be decomposed into wave frequency bands and/or frequency power levels using Fourier Transformation. In an example, parameters used to identify a pattern of electromagnetic brain activity can be selected from the group consisting of: power level, amplitude, maximum value, minimum value, frequency, phase, covariation, entropy, latency, and waveform. In an example, a change in an already-occurring repeating brainwave can be a change in the amplitude, power level, minimum value, and/or maximum value of activity within one or more selected frequency bands. In an example, a change in an already-occurring repeating brainwave can be a shift in the frequency or phase of a waveform within one or more selected frequency bands. In an example, a change in an already-occurring repeating brainwave can be a change in the shape of a waveform within one or more selected frequency bands.

In an example, a change in an already-occurring repeating brainwave can be a change in the amplitude, power level, minimum value, and/or maximum value of activity within a selected frequency band relative to one or more other frequency bands. In an example, a change in an already-occurring repeating brainwave can be a shift in the frequency or phase of a waveform within a selected frequency band relative to one or more other frequency bands. In an example, a change in an already-occurring repeating brainwave can be a change in the shape of a waveform within a selected frequency band relative to one or more other frequency bands. In an example, a change in an already-occurring repeating brainwave can be a change in the covariation of activity in a selected frequency band relative to activity in another frequency band.

In an example, a pattern of electromagnetic brain activity which is associated with an action to control an environmental device can be associated with a particular sensor location, a particular channel, and/or particular montage of channels. In an example, a pattern of electromagnetic brain activity can be a change in activity in a specific area of a person's brain as measured from one or more specific sensor locations on the person's head. In an example, this pattern can be a transient pattern which is recorded from one or more locations. In an example, this pattern can be the start of a repeating pattern which is recorded from one or more locations. In an example, this pattern can be a change in an ongoing repeating pattern which is recorded from one or more locations. In an example, this pattern can be a change in electromagnetic brain activity measured from one location or channel relative to electromagnetic brain activity measured from one or more different locations or channels. In an example, which channels are most useful for identifying a pattern of electromagnetic brain activity associated with an action to control an environmental device can be identified during a calibration period. In an example, different channels can be most useful for pattern identification at different times during an action.

In an example, one or more electromagnetic brain activity sensors or channels can be located on a person's head so as to most accurately measure the activity of one or more brain areas selected from the group consisting of: Broca's area (of the Frontal Lobe), Wernicke's area (of the Occipital Lobe), Cerebellum, Cerebral Cortex, Frontal Lobe, Occipital Lobe, Parietal Lobe, and Temporal Lobe. In an example, one or more electromagnetic brain activity sensors or channels can be placed at one or more electrode placement sites selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

We now discuss the specific examples shown in FIGS. 9 through 16. FIGS. 9 through 12 show an example of how this invention can be embodied in a Brain Computer Interface (BCI) method which enables a person to control environmental devices, appliances, and/or machines in different action modes based on electromagnetic brain activity patterns which are associated with the same control command across different action modes. One or more action modes can be selected from the group consisting of: speaking a word, phrase, or command; using a touch screen; manually moving a switch, button, dial, or knob on an environmental device; making a hand gesture; typing a word, phrase, or command; moving a computer mouse; moving one's eyes; and just thinking about controlling the environmental device. In this example, three action modes are used: (a) speaking a word, phrase, or command; (b) using a touch screen; and (c) just thinking about controlling the environmental device. The first two action modes (speaking and touching) are used during first and second calibration time periods and the third action mode (thinking alone) is used in a third time period.

Figure 9:
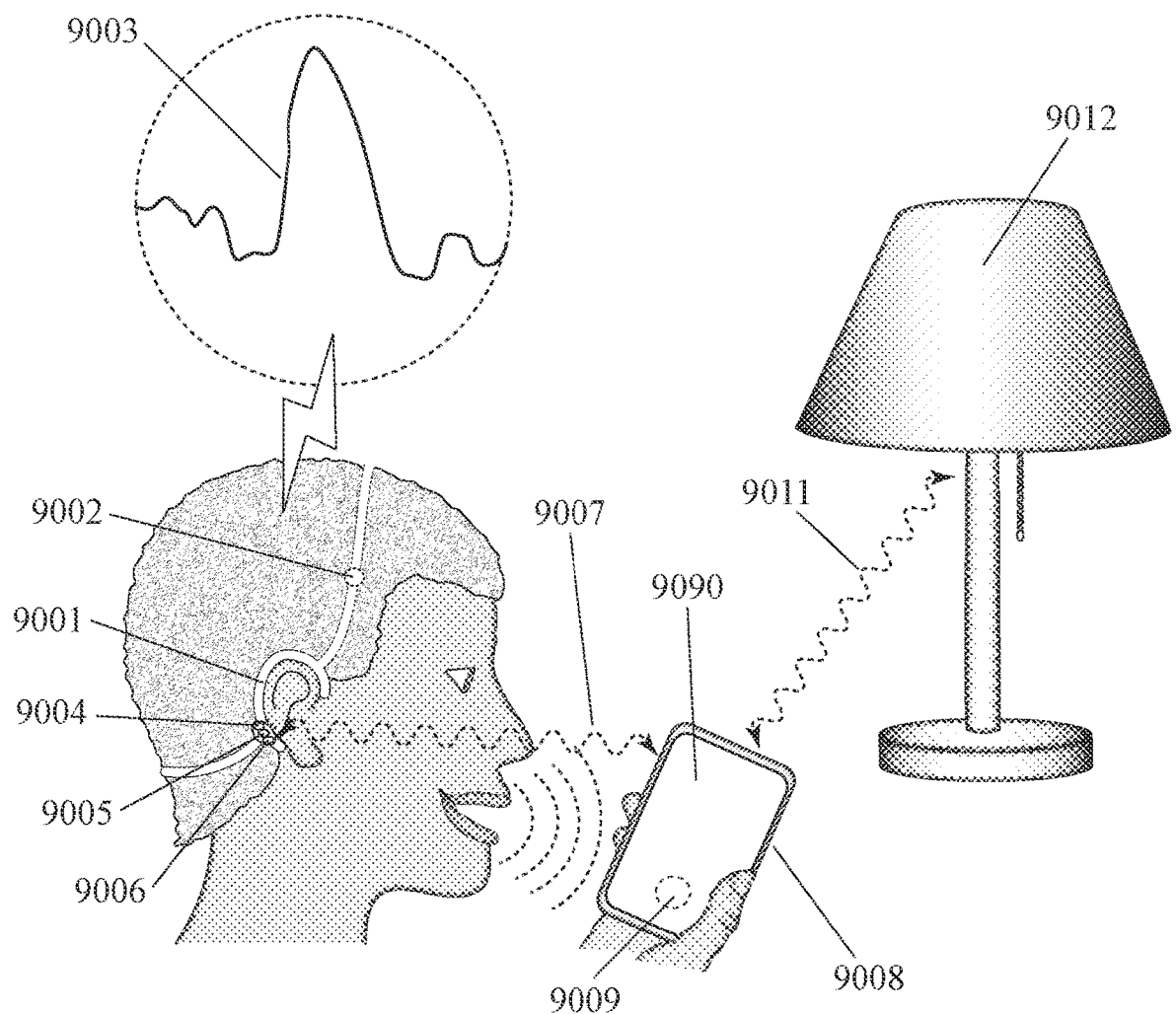
FIG. 9 shows a BCI system and method in which a person controls an environmental device using a first command mode (voice).
Figure 10:
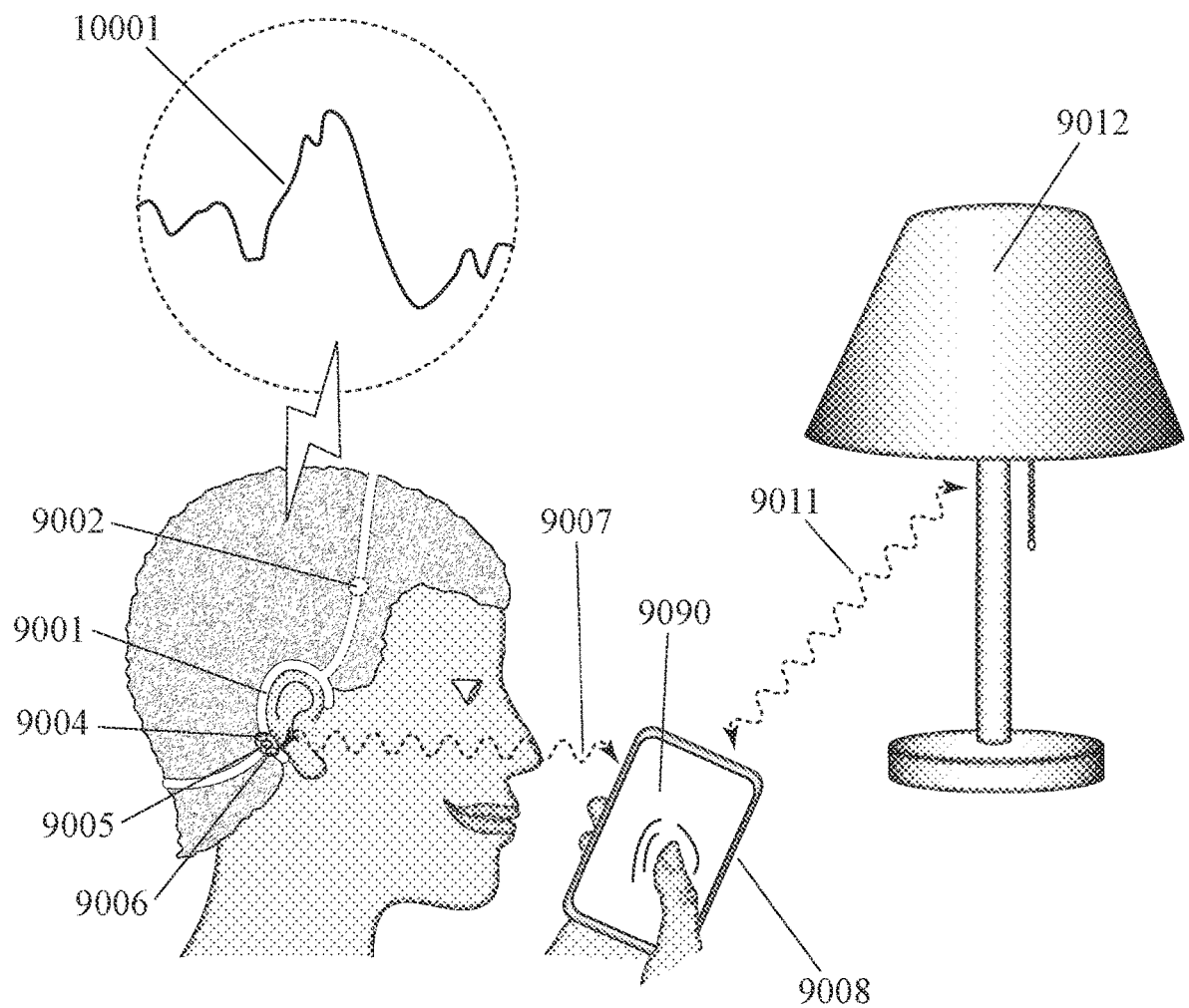
FIG. 10 shows a BCI system and method in which a person controls an environmental device using a second command mode (touch screen).
Figure 11:
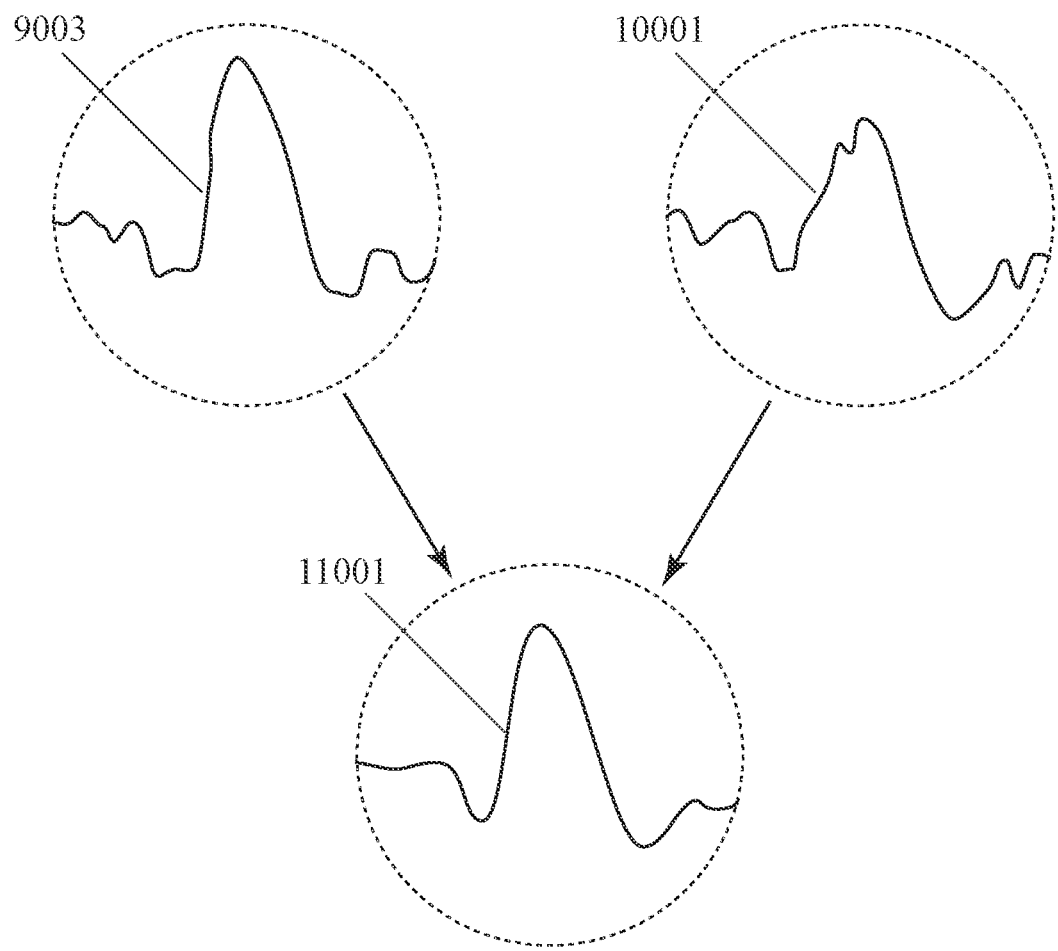
FIG. 11 shows a BCI system and method wherein a common brain activity pattern between the first and second command modes is identified.
Figure 12:
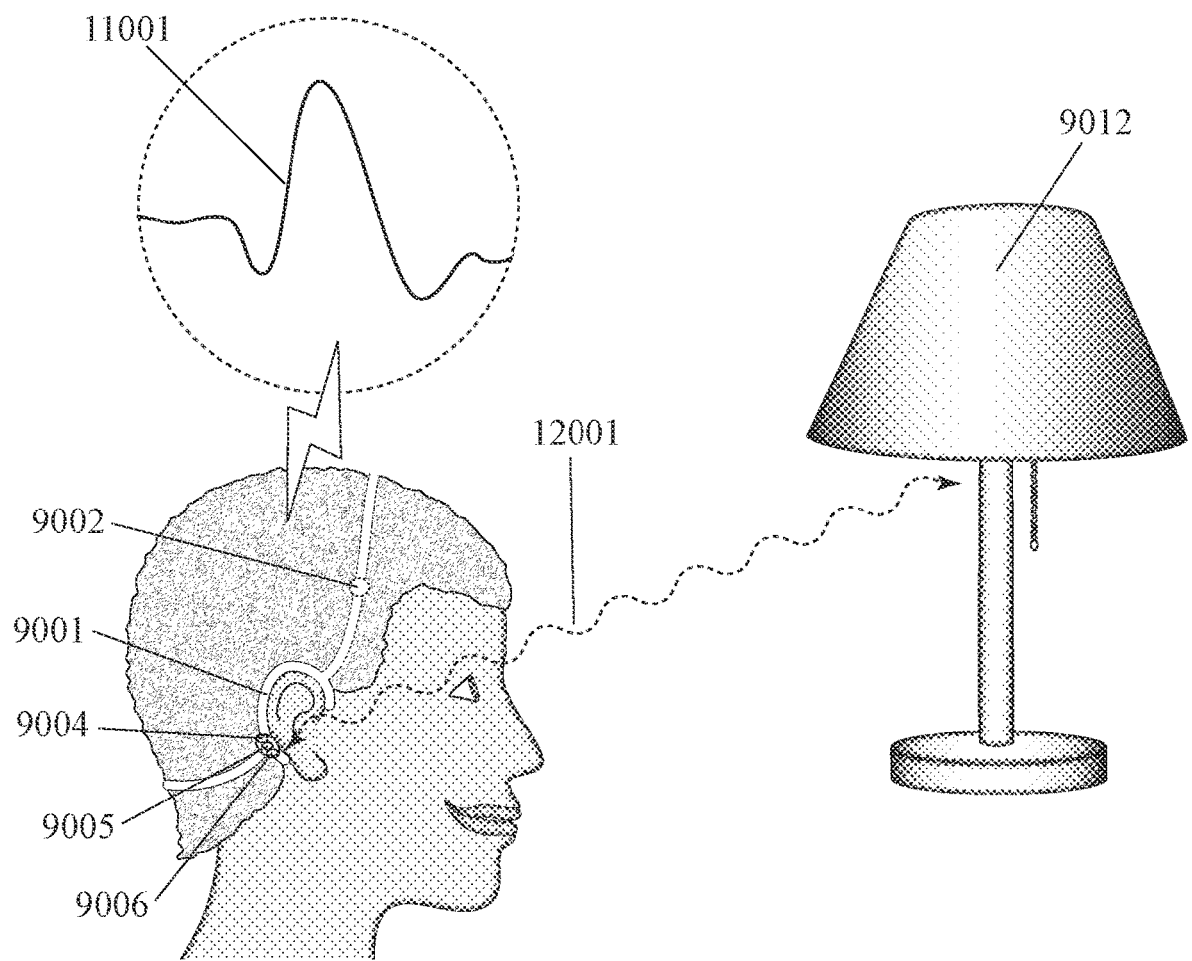
FIG. 12 shows a BCI system and method in which a person controls an environmental device using a third command mode (thought).

FIGS. 9 through 12 are sequential views of the same embodiment. FIGS. 9 through 12 show both a system and a method. FIG. 9 shows this embodiment during a first calibration time period in which a person controls an environmental device (a lamp in this example) in a selected manner by speaking a word, phrase, or command, while an electromagnetic brain activity sensor collects a first set of data concerning the person's brain activity which is associated with this action. FIG. 10 shows this embodiment during a second calibration time period in which the person controls the environmental device (the lamp) in the selected manner by touching a touch screen on a separate hand-held device, while the electromagnetic brain activity sensor collects a second set of data concerning the person's brain activity associated with this action. FIG. 11 symbolically represents how the data processing unit analyzes the first and second sets of data in order to indentify a common pattern of electromagnetic brain activity (e.g. which is found in both sets of data). FIG. 12 shows this embodiment during a third period of time in which the data processing unit recognizes this common pattern in the person's electromagnetic brain activity (because the person is thinking about controlling the device) and controls the environmental device in the selected manner even though the person is not speaking or using the touch screen.

With respect to specific components of this Brain Computer Interface (BCI) system, FIG. 9 shows: a head-worn attachment 9001 which is worn on the person's head; at least one electromagnetic brain activity sensor 9002 which is part of the head-worn attachment member; a first electromagnetic brain activity pattern 9003 which is measured by the at least one electromagnetic brain activity sensor during this time period; a data processing unit 9004; a data transmitter and receiver 9005; a microphone 9006 on the head-worn attachment; wireless communication 9007 between the data processing unit and a separate hand-held computing device; the separate hand-held computing device 9008; a microphone 9009 on the hand-held computing device; a touch screen 9010 on the separate hand-held computing device; wireless communication 9011 between the separate hand-held computing device and an environmental device (a lamp in this example); and an environmental device 9012 (a lamp in this example).

In the example shown in FIGS. 9 through 12, this invention is a system comprising two separate devices which function together. The first device is worn on the head and the second device is held in a hand. In another example of a system, the second device can be worn on a different location on the body. In another example, the second device can be a smart watch or wearable technology hub. In another example, this invention can be a self-contained head-worn device with all the components and performing all the functions.

In FIG. 9, the person is controlling the lamp via a first action mode—speaking a command. For example, the person can say "Light On." This command is received by a microphone, understood by speech recognition software, and becomes a command to turn the lamp on via wireless communication. In FIG. 9, the electromagnetic brain activity sensor measures a pattern 9003 of electromagnetic brain activity which is associated with speaking this command. This pattern of brain activity is symbolically represented by the wavy line within a dotted line circle above the person's head.

FIG. 10 is like FIG. 9 except that now the person is controlling the lamp via a second action mode—using a touch screen. For example, the person can open an application on the hand-held device and touch an icon to turn the light on via wireless communication. In FIG. 10, the electromagnetic brain activity sensor measures a pattern 10001 of electromagnetic brain activity which is associated with using the touch screen in this manner. This pattern of brain activity is symbolically represented by the wavy line within a dotted line circle above the person's head. Note that the details of electromagnetic brain activity pattern 10001 are different than the details of electromagnetic brain activity pattern 9003, but that there are some similarities between these two patterns. These pattern similarities can be due to common underlying mental processes which are involved in different actions to turn on a light, regardless of the specific mode of action through which this is done.

FIG. 11 shows a symbolic representation of a step wherein the data processing unit analyzes electromagnetic brain activity pattern 9003 and electromagnetic brain activity pattern 10001 in order to identify a common pattern which they both share. In FIG. 11, this common pattern 11001 is shown within a dotted-line circle at the bottom of the figure. In an example, a common pattern can be identified using one or more statistical methods selected from the group consisting of: Analysis of Variance (ANOVA), Artificial Neural Network (ANN), Auto-Regressive (AR) Modeling, Bayesian Analysis, Bonferroni Analysis (BA), Centroid Analysis, Chi-Squared Analysis, Cluster Analysis, Correlation, Covariance, Data Normalization (DN), Decision Tree Analysis (DTA), Discrete Fourier transform (DFT), Discriminant Analysis (DA), Empirical Mode Decomposition (EMD), Factor Analysis (FA), Fast Fourier Transform (FFT), Feature Vector Analysis (FVA), Fisher Linear Discriminant, Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inter-Band Power Ratio, Inter-Channel Power Ratio, Inter-Montage Power Mean, Inter-Montage Ratio, Kalman Filter (KF), Kernel Estimation, Laplacian Filter, Laplacian Montage Analysis, Least Squares Estimation, Linear Regression, Linear Transform, Logit Model, Machine Learning (ML), Markov Model, Maximum Entropy Modeling, Maximum Likelihood, Mean Power, Monkey Darts (MD), Multi-Band Covariance Analysis, Multi-Channel Covariance Analysis, Multivariate Linear Regression, Multivariate Logit, Multivariate Regression, Naive Bayes Classifier, Neural Network, Non-Linear Programming, Non-negative Matrix Factorization (NMF), Power Spectral Density, Power Spectrum Analysis, Principal Components Analysis (PCA), Probit Model, Quadratic Minimum Distance Classifier, Random Forest (RF), Random Forest Analysis (RFA), Regression Model, Signal Amplitude (SA), Signal Averaging, Signal Decomposition, Sine Wave Compositing, Singular Value Decomposition (SVD), Spine Function, Support Vector Machine (SVM), Time Domain Analysis, Time Frequency Analysis, Time Series Model, Trained Bayes Classifier, Variance, Waveform Identification, Wavelet Analysis, and Wavelet Transformation.

FIG. 12 is like FIGS. 9 and 10 except that now the person is controlling the lamp without either speaking or using the touch screen. In this example, the person is now turning on the lamp by just thinking about turning on the lamp. This thought is identified by the data processing unit based on detection of the common electromagnetic brain activity pattern 11001 which is associated with turning on the lamp by either speaking or using the touch screen. This common pattern is detected and triggers a command via wireless communication 12001 from the data processing unit (via data transmitter) to the lamp. Other relevant component and method variations which are discussed elsewhere in this specification can also be applied to the example shown here in FIGS. 9 through 12.

FIGS. 13 through 16 show another example of how this invention can be embodied in a Brain Computer Interface (BCI) system, device, and method which enables a person to control environmental devices, appliances, and/or machines in different action modes based on electromagnetic brain activity patterns which are associated with the same control command across different action modes. This example is like the one shown in FIGS. 9 through 12 except that now speech recognition occurs within a head-worn component instead of a hand-held device.

Figure 13:
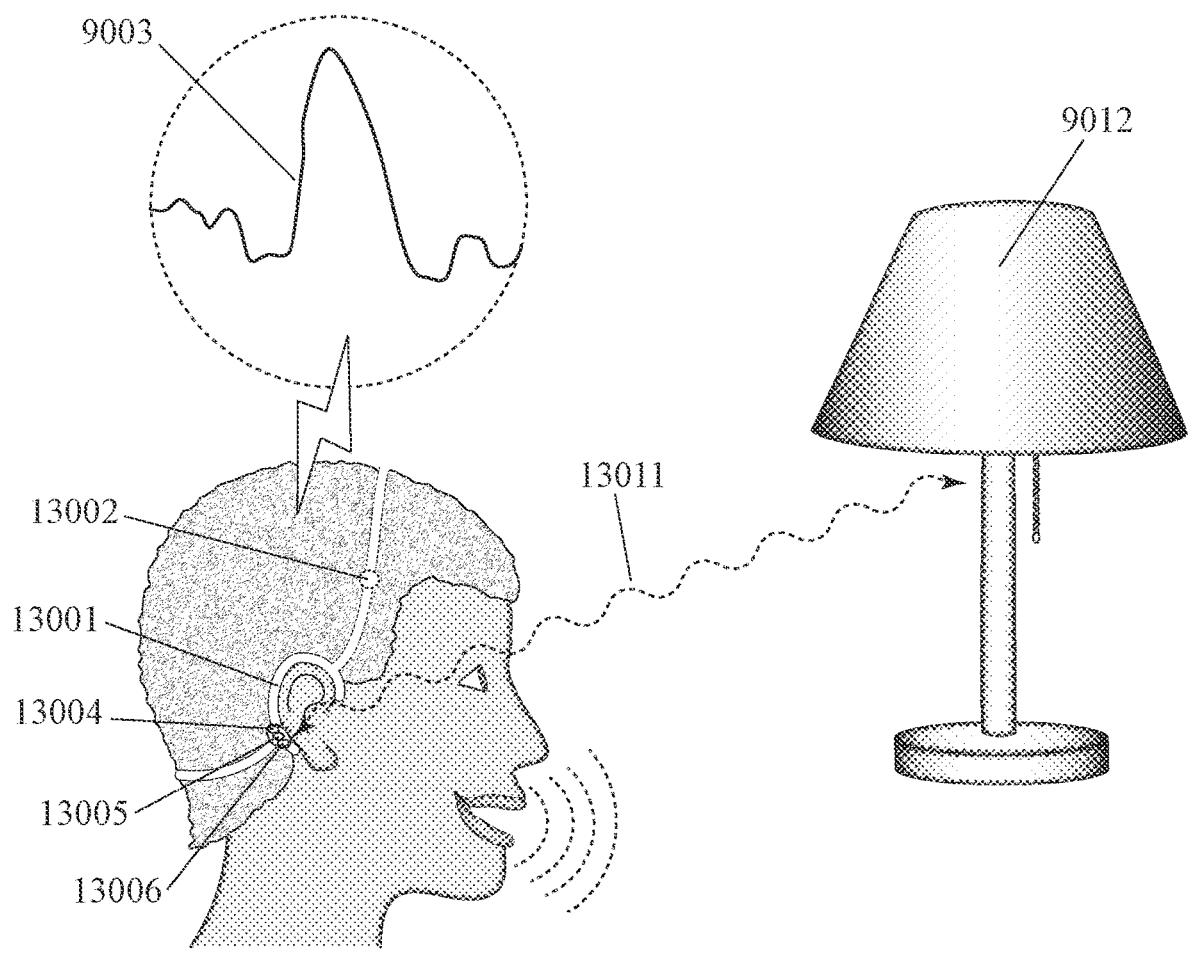
FIG. 13 shows another example of a BCI system and method in which a person controls an environmental device using a first command mode (voice).
Figure 14:
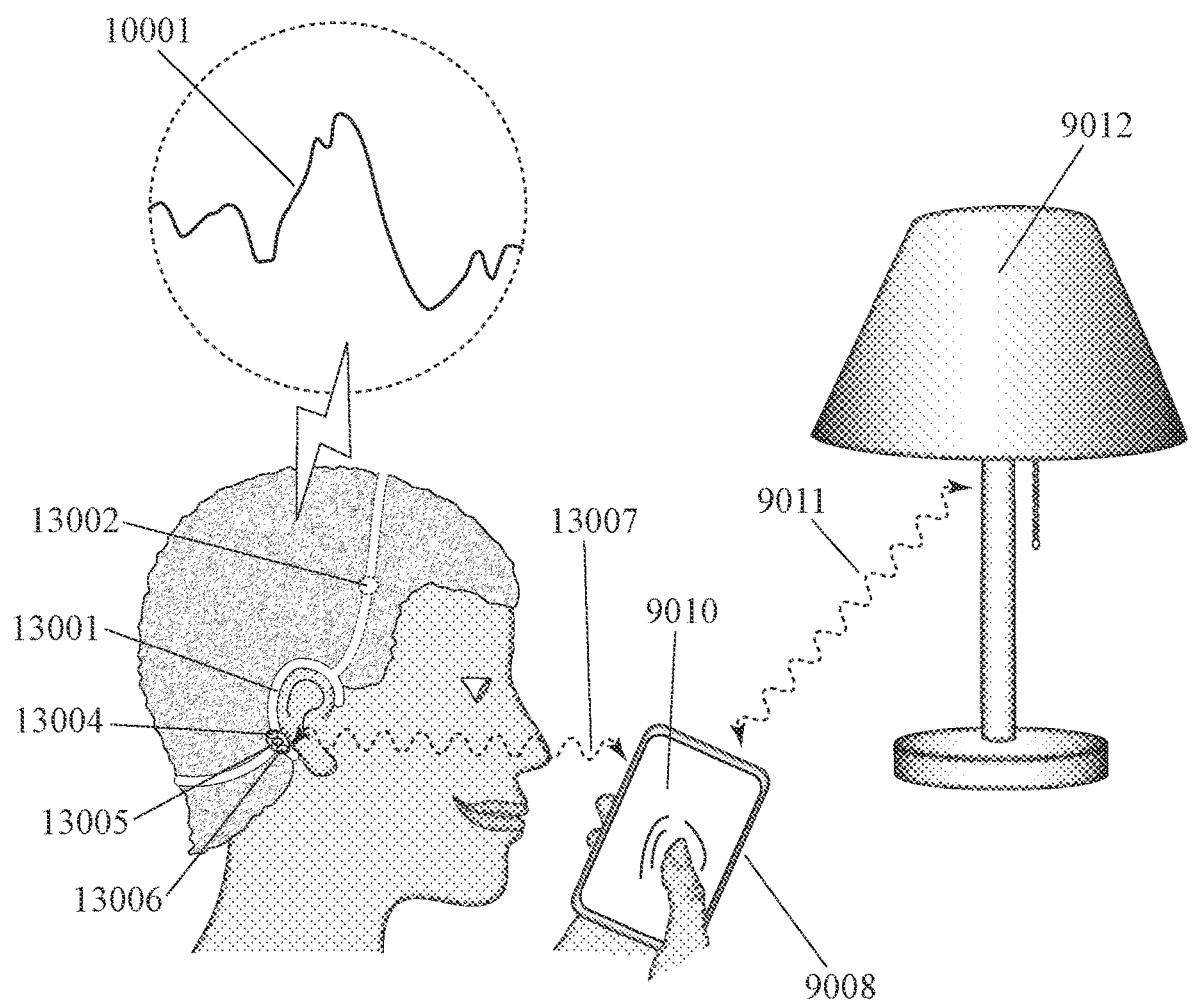
FIG. 14 shows another example of a BCI system and method in which a person controls an environmental device using a second command mode (touch screen).
Figure 15:
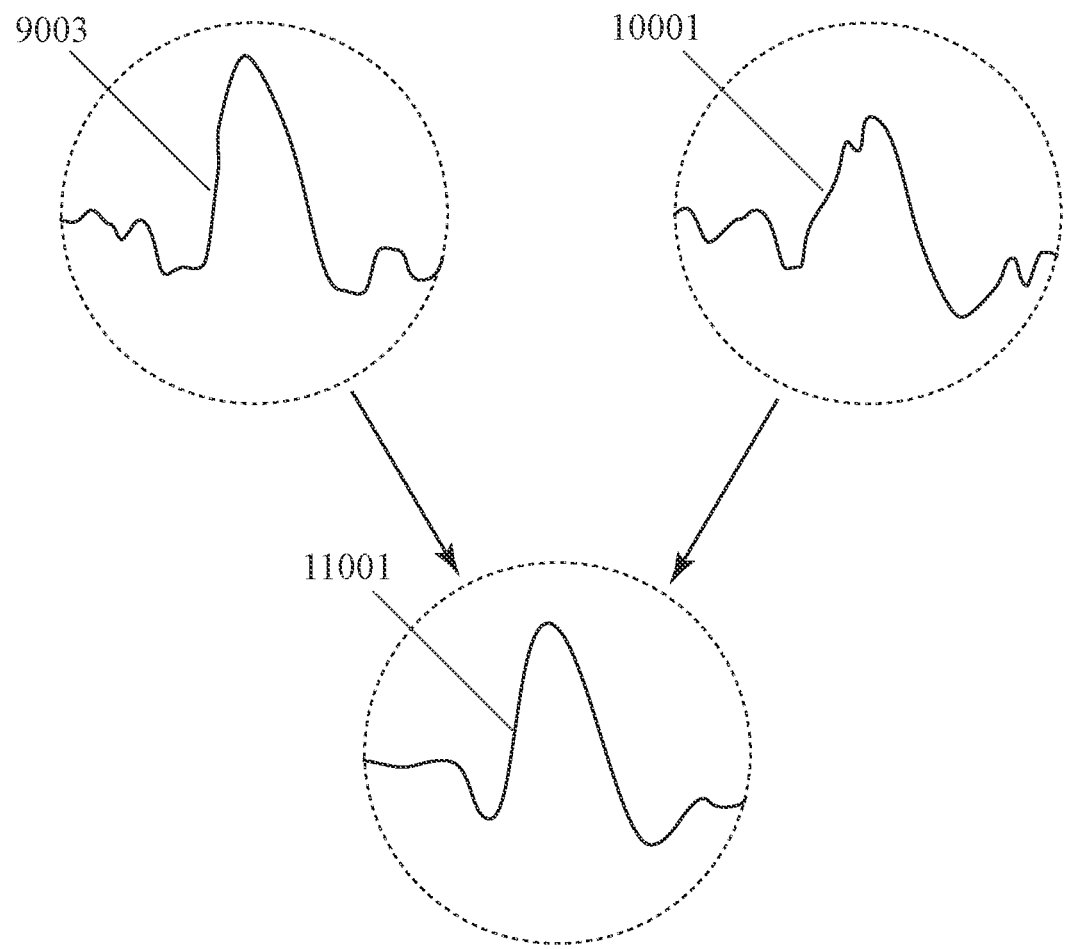
FIG. 15 shows another example of a BCI system and method wherein a common brain activity pattern between the first and second command modes is identified.
Figure 16:
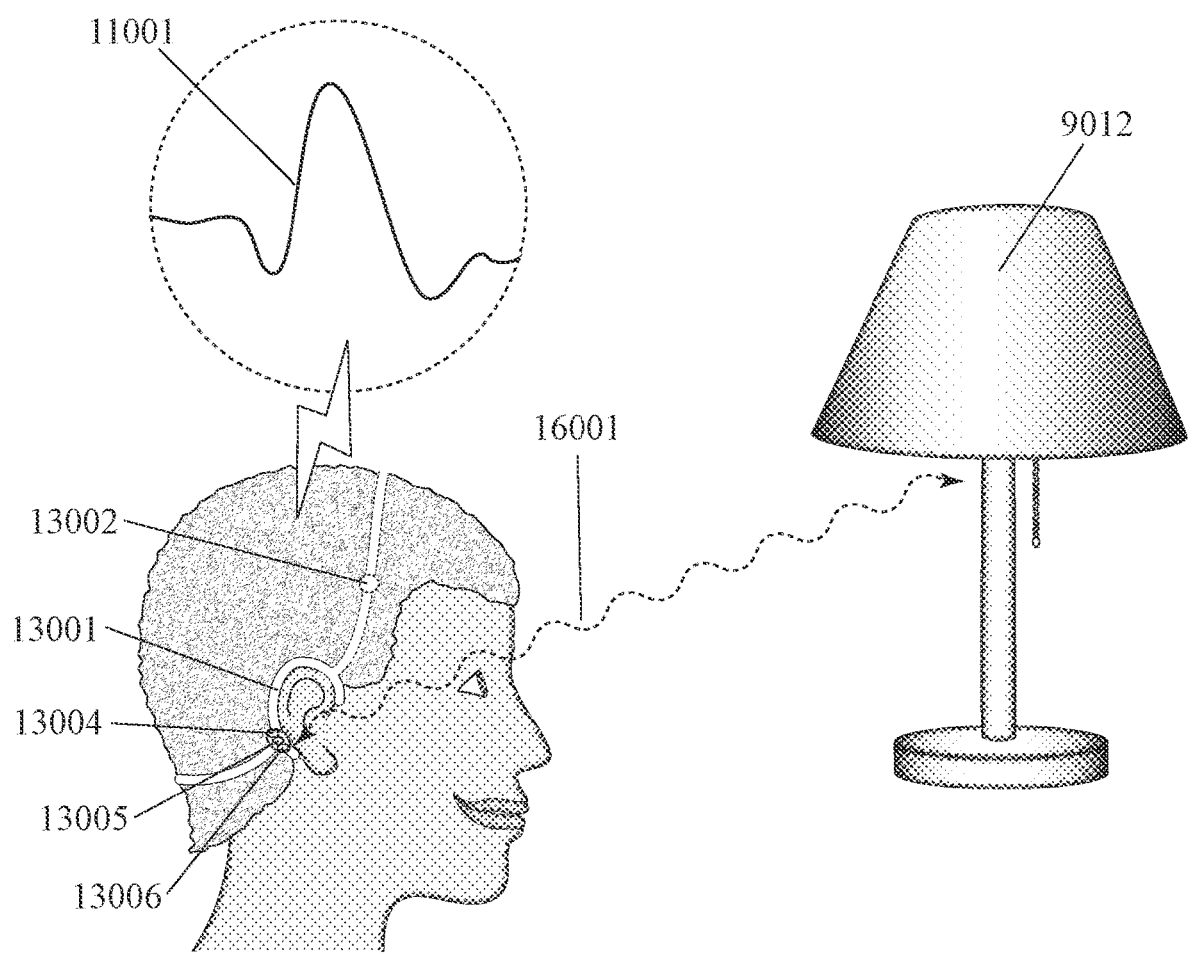
FIG. 16 shows another example of a BCI system and method in which a person controls an environmental device using a third command mode (thought).

FIGS. 13 through 16 are sequential views of the same embodiment. FIGS. 13 through 16 show both a system and a method. FIG. 13 shows this embodiment during a first calibration time period in which a person controls an environmental device (a lamp in this example) in a selected manner by speaking a word, phrase, or command, while an electromagnetic brain activity sensor collects a first set of data concerning the person's brain activity which is associated with this action. FIG. 14 shows this embodiment during a second calibration time period in which the person controls the environmental device (the lamp) in the selected manner by touching a touch screen on a separate hand-held device, while the electromagnetic brain activity sensor collects a second set of data concerning the person's brain activity associated with this action. FIG. 15 symbolically represents how the data processing unit analyzes the first and second sets of data in order to indentify a common pattern of electromagnetic brain activity (e.g. which is found in both sets of data). FIG. 16 shows this embodiment during a third period of time in which the data processing unit recognizes this common pattern in the person's electromagnetic brain activity (because the person is thinking about controlling the device) and controls the environmental device in the selected manner even though the person is not speaking or using the touch screen.

With respect to specific components of this Brain Computer Interface (BCI) system, FIG. 13 shows: a head-worn attachment 13001 which is worn on the person's head; at least one electromagnetic brain activity sensor 13002 which is part of the head-worn attachment member; a first electromagnetic brain activity pattern 13003 which is measured by the at least one electromagnetic brain activity sensor during this time period; a data processing unit 13004; a data transmitter and receiver 13005; a microphone 13006; wireless communication 13011 between the separate hand-held computing device and an environmental device (a lamp in this example); and an environmental device 9012 (a lamp in this example).

In FIG. 13, the person is controlling the lamp via a first action mode—speaking a command. For example, the person can say "Light On." This is received by the microphone, understood by speech recognition software, and becomes a command to turn the lamp on via wireless communication. In FIG. 13, the electromagnetic brain activity sensor measures a pattern 9003 of electromagnetic brain activity which is associated with speaking this command. This pattern of brain activity is symbolically represented by the wavy line within a dotted line circle above the person's head.

FIG. 14 is like FIG. 13 except that now the person is controlling the lamp via a second action mode—using a touch screen. For example, the person can open an application on the hand-held device and touch an icon to turn the light on via wireless communication. In FIG. 14, the electromagnetic brain activity sensor measures a pattern 10001 of electromagnetic brain activity which is associated with using the touch screen in this manner. This pattern of brain activity is symbolically represented by the wavy line within a dotted line circle above the person's head. Note that the details of electromagnetic brain activity pattern 10001 are different than the details of electromagnetic brain activity pattern 9003, but that there are some similarities between these two patterns. These pattern similarities can be due to common underlying mental processes which are involved in different actions to turn on a light, regardless of the specific mode of action through which this is done.

FIG. 15 shows a symbolic representation of a step wherein the data processing unit analyzes electromagnetic brain activity pattern 9003 and electromagnetic brain activity pattern 10001 in order to identify a common pattern which they both share. In FIG. 15, this common pattern 11001 is shown within a dotted-line circle at the bottom of the figure.

FIG. 16 is like FIGS. 13 and 14 except that now the person is controlling the lamp without either speaking or using the touch screen. In this example, the person is now turning on the lamp by just thinking about turning on the lamp. This thought is identified by the data processing unit based on detection of the common electromagnetic brain activity pattern 11001 which is associated with turning on the lamp by either speaking or using the touch screen. This common pattern is detected and triggers a command via wireless communication 16001 from the data processing unit (via data transmitter) to the lamp. Other relevant component and method variations which are discussed elsewhere in this specification can also be applied to the example shown here in FIGS. 13 through 16.

In an example, this invention can be embodied in a Brain Computer Interface (BCI) system, device, or method which enables a person to control environmental devices, appliances, and/or machines in different action modes based on brain activity patterns which are associated with the same control command across different action modes. In these various examples, one or more action modes can be selected from the group consisting of: speaking a word, phrase, or command; using a touch screen; manually moving a switch, button, dial, or knob on an environmental device, appliance, and/or machine; making a hand gesture; typing a word, phrase, or command; moving a computer mouse; moving one's eyes; and just thinking about controlling an environmental device, appliance, and/or machine.

In an example, a method for interpreting a person's electromagnetic brain activity to control and/or communicate with a device in the person's environment can comprise: (a) receiving data concerning a person's electromagnetic brain activity during a first time period in which the person uses a first action modality to control a device in the person's environment in a selected manner or communicate a selected word or phrase to the device; wherein the first action modality is selected from the group consisting of: using a touch screen; typing a word, phrase, or command; moving a computer mouse; speaking a word, phrase, or command; manually moving a switch, button, dial, or knob on the environmental device; making a hand gesture; moving their eyes; and just thinking about controlling the environmental device; (b) receiving data concerning the person's electromagnetic brain activity during a second time period in which the person uses a second action modality to control the device in the person's environment in the selected manner or communicate the selected word or phrase to the device; wherein the second action modality is selected from the group consisting of: using a touch screen; typing a word, phrase, or command; moving a computer mouse; speaking a word, phrase, or command; manually moving a switch, button, dial, or knob on the environmental device; making a hand gesture; moving their eyes; and just thinking about controlling the environmental device; and wherein the second action modality is different than the first action modality; (c) analyzing the data from the first time period and the second time period to identify a specific pattern of electromagnetic brain activity in both the first time period and the second time period; wherein this specific pattern of electromagnetic brain activity is associated with controlling the device in the person's environment in the selected manner or communicating the selected word or phrase to the device; (d) receiving data concerning the person's electromagnetic brain activity during a third time period in which the person does not use either the first action modality or the second action modality; (e) analyzing the data from the third time period to identify the specific pattern of electromagnetic brain activity which is associated with controlling the device in the person's environment in the selected manner or communicating the selected word or phrase to the device; and (f) controlling the device in the person's environment in the selected manner or communicating the selected word or phrase to the device when the specific pattern is identified during the third time period.

In an example, the first action modality is using a touch screen. In an example, the first action modality is using a typing a word, phrase, or command. In an example, the first action modality is moving a computer mouse. In an example, the first action modality is speaking a word, phrase, or command. In an example, the first action modality is manually moving a switch, button, dial, or knob on the environmental device. In an example, the first action modality is making a hand gesture. In an example, the first action modality is moving their eyes. In an example, the first action modality is just thinking about controlling the environmental device.

In an example, a method for interpreting a person's electromagnetic brain activity to control and/or communicate with a device in the person's environment can comprise: (a) receiving data concerning a person's electromagnetic brain activity during a first time period in which the person uses a first action modality to control a device in the person's environment in a selected manner or communicate a selected word or phrase to the device; wherein the first action modality is selected from the group consisting of: using a touch screen; typing a word, phrase, or command; moving a computer mouse; speaking a word, phrase, or command; manually moving a switch, button, dial, or knob on the environmental device; making a hand gesture; the person moving their eyes; and just thinking about controlling the environmental device; (b) receiving data concerning the person's electromagnetic brain activity during a second time period in which the person uses a second action modality to control the device in the person's environment in the selected manner or communicate the selected word or phrase to the device; wherein the second action modality is selected from the group consisting of: using a touch screen; typing a word, phrase, or command; moving a computer mouse; speaking a word, phrase, or command; manually moving a switch, button, dial, or knob on the environmental device; making a hand gesture; the person moving their eyes; and just thinking about controlling the environmental device; and wherein the second action modality is different than the first action modality; (c) analyzing the data from the first time period and the second time period to identify a specific pattern of electromagnetic brain activity in both the first time period and the second time period; wherein this specific pattern of electromagnetic brain activity is associated with controlling the device in the person's environment in the selected manner or communicating the selected word or phrase to the device; (d) receiving data concerning the person's electromagnetic brain activity during a third time period in which the person just thinks about controlling the device in the person's environment in the selected manner or communicating the selected word or phrase to the device; and wherein the person does not use an action modality is selected from the group consisting of: using a touch screen; typing a word, phrase, or command; moving a computer mouse; speaking a word, phrase, or command; manually moving a switch, button, dial, or knob on the environmental device; making a hand gesture; and moving their eyes; (e) analyzing the data from the third time period to identify the specific pattern of electromagnetic brain activity which is associated with controlling the device in the person's environment in the selected manner or communicating the selected word or phrase to the device; and (f) controlling the device in the person's environment in the selected manner or communicating the selected word or phrase to the device when the specific pattern is identified during the third time period.

In an example, the first action modality is using a touch screen. In an example, the first action modality is using a typing a word, phrase, or command. In an example, the first action modality is moving a computer mouse. In an example, the first action modality is speaking a word, phrase, or command. In an example, the first action modality is manually moving a switch, button, dial, or knob on the environmental device. In an example, the first action modality is making a hand gesture. In an example, the first action modality is moving their eyes. In an example, the first action modality is just thinking about controlling the environmental device. In an example, the first action modality is using a touch screen or typing on a keyboard and the second action modality is speaking a word, phrase, or command. In an example, the first action modality is using a touch screen or typing on a keyboard and the second action modality is manually moving a switch, button, dial, or knob on the environmental device.

I claim:

1. A method for interpreting a person's electromagnetic brain activity to control a device in the person's environment:

receiving electromagnetic brain activity data recorded by EEG sensors worn by a person during a first time period in which the person uses a first action modality to make a selected command to control a device in the person's environment; wherein the first action modality is selected from the group consisting of: using a touch screen; typing a word, phrase, or command; moving a computer mouse; speaking a word, phrase, or command; manually moving a switch, button, dial, or knob on the device in the person's environment; making a hand gesture; eye movement; and only thinking about making the selected command;

receiving electromagnetic brain activity data recorded by EEG sensors worn by the person during a second time period in which the person uses a second action modality to make the selected command to control the device in the person's environment; wherein the second action modality is selected from the group consisting of: using a touch screen; typing a word, phrase, or command; moving a computer mouse; speaking a word, phrase, or command; manually moving a switch, button, dial, or knob on the device in the person's environment; making a hand gesture; eye movement; and only thinking about making the selected command or communicating the selected word or phrase; and wherein the second action modality is different than the first action modality;

analyzing the electromagnetic brain activity data recorded by the EEG sensors worn by the person from the first time period and the electromagnetic brain activity data recorded by the EEG sensors worn by the person from the second time period to identify a specific pattern of electromagnetic brain activity which is common to both the first time period and the second time period; wherein the specific pattern of electromagnetic brain activity is associated with making the selected command; and wherein the electromagnetic brain activity data is analyzed in a data processor using one or more methods selected from the group consisting of: Analysis of Variance (ANOVA), Artificial Neural Network (ANN), Auto-Regressive (AR) Modeling, Bayesian Analysis, Bonferroni Analysis (BA), Centroid Analysis, Chi-Squared Analysis, Cluster Analysis, Correlation, Covariance, Data Normalization (DN), Decision Tree Analysis (DTA), Discrete Fourier transform (DFT), Discriminant Analysis (DA), Empirical Mode Decomposition (EMD), Factor Analysis (FA), Fast Fourier Transform (FFT), Feature Vector Analysis (FVA), Fisher Linear Discriminant, Fourier Transformation (FT), Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inter-Band Power Ratio, Inter-Channel Power Ratio, Inter-Montage Power Mean, Inter-Montage Ratio, Kalman Filter (KF), Kernel Estimation, Laplacian Filter, Laplacian Montage Analysis, Least Squares Estimation, Linear Regression, Linear Transform, Logit Model, Machine Learning (ML), Markov Model, Maximum Entropy Modeling, Maximum Likelihood, Mean Power, Multi-Band Covariance Analysis, Multi-Channel Covariance Analysis, Multivariate Linear Regression, Multivariate Logit, Multivariate Regression, Naive Bayes Classifier, Neural Network, Non-Linear Programming, Non-negative Matrix Factorization (NMF), Power Spectral Density, Power Spectrum Analysis, Principal Components Analysis (PCA), Probit Model, Quadratic Minimum Distance Classifier, Random Forest (RF), Random Forest Analysis (RFA), Regression Model, Signal Amplitude (SA), Signal Averaging, Signal Decomposition, Sine Wave Compositing, Singular Value Decomposition (SVD), Spine Function, Support Vector Machine (SVM), Time Domain Analysis, Time Frequency Analysis, Time Series Model, Trained Bayes Classifier, Variance, Waveform Identification, Wavelet Analysis, and Wavelet Transformation;

receiving data recorded by EEG sensors worn by the person during a third time period in which the person only thinks about making the selected command to control the device in the person's environment; and wherein during the third time period the person does not use any action modality selected from the group consisting of: using a touch screen; typing a word, phrase, or command; moving a computer mouse; speaking a word, phrase, or command; manually moving a switch, button, dial, or knob on the device in the person's environment; making a hand gesture; and eye movement;

analyzing the electromagnetic brain activity data recorded by EEG sensors worn by the person from the third time period to identify whether the specific pattern of electromagnetic brain activity which is associated with the selected command has occurred during the third time period; and automatically transmitting the selected command to a device in the person's environment if the specific pattern is identified as occurring during the third time period.

2. The method in claim 1 wherein the first action modality is using a touch screen.

3. The method in claim 1 wherein the first action modality is using a typing a word, phrase, or command.

4. The method in claim 1 wherein the first action modality is moving a computer mouse.

5. The method in claim 1 wherein the first action modality is speaking a word, phrase, or command.

6. The method in claim 1 wherein the first action modality is manually moving a switch, button, dial, or knob on the device in the person's environment.

7. The method in claim 1 wherein the first action modality is making a hand gesture.

8. The method in claim 1 wherein the first action modality is eye movement.

9. The method in claim 1 wherein the first action modality is using a touch screen or typing on a keyboard and the second action modality is speaking a word, phrase, or command.

10. The method in claim 1 wherein the first action modality is using a touch screen or typing on a keyboard and the second action modality is manually moving a switch, button, dial, or knob on the device in the person's environment.

* * * * *